US008582099B2

(12) United States Patent  (10) Patent No.: US 8,582,099 B2
Guo et al.  (45) Date of Patent: Nov. 12, 2013

(54) MONITORING NETWORK BASED ON NANO-STRUCTURED SENSING DEVICES

(75) Inventors: Xun Guo, Sacramento, CA (US); Hong Wang, Cupertino, CA (US); Chunwei Liu, Jiangsu (CN)

(73) Assignee: OptoTrace Technologies, Inc., Mountain View, CA (US)

( * ) Notice: Subject to any disclaimer, the term of this patent is extended or adjusted under 35 U.S.C. 154(b) by 402 days.

(21) Appl. No.: 13/080,142

(22) Filed: Apr. 5, 2011

(65) Prior Publication Data

US 2011/0212512 A1  Sep. 1, 2011

Related U.S. Application Data

(63) Continuation-in-part of application No. 12/502,903, filed on Jul. 14, 2009, now Pat. No. 7,929,133, which is a continuation of application No. 12/262,667, filed on Oct. 31, 2008, now Pat. No. 7,576,854, which is a continuation of application No. 11/562,409, filed on Nov. 21, 2006, now Pat. No. 7,460,224, application No. 13/080,142, which is a continuation-in-part of application No. 12/625,970, filed on Nov. 25, 2009, now Pat. No. 8,213,007, which is a continuation-in-part of application No. 12/403,522, filed on Mar. 13, 2009, now Pat. No. 8,102,525, application No. 13/080,142, which is a continuation-in-part of application No. 12/643,689, filed on Dec. 21, 2009, now Pat. No. 8,081,308.

(60) Provisional application No. 60/751,472, filed on Dec. 19, 2005.

(51) Int. Cl.
*G01J 3/28* (2006.01)

(52) U.S. Cl.
USPC .......................................... 356/326; 356/301

(58) Field of Classification Search
USPC .................................................. 356/301, 326
See application file for complete search history.

(56) References Cited

U.S. PATENT DOCUMENTS

| 5,210,590 | A | * | 5/1993 | Landa et al. ................... 356/328 |
| 5,455,673 | A | * | 10/1995 | Alsmeyer et al. ............. 356/301 |
| 2003/0142309 | A1 | * | 7/2003 | Kuebler et al. ................ 356/338 |
| 2005/0162646 | A1 | * | 7/2005 | Tedesco et al. ................ 356/301 |
| 2006/0055922 | A1 | | 3/2006 | Li |
| 2006/0164634 | A1 | | 7/2006 | Kamins |
| 2006/0209300 | A1 | | 9/2006 | Kamins |
| 2006/0279732 | A1 | | 12/2006 | Wang |
| 2007/0056388 | A1 | * | 3/2007 | Henry et al. ................ 73/863.12 |
| 2007/0177139 | A1 | | 8/2007 | Kamins |
| 2007/0233401 | A1 | | 10/2007 | Workman |
| 2007/0252979 | A1 | | 11/2007 | Bratkovski |
| 2010/0209004 | A1 | | 8/2010 | Potuluri |

* cited by examiner

*Primary Examiner* — Kara E Geisel

(74) *Attorney, Agent, or Firm* — SV Patent Service

(57) ABSTRACT

A monitoring network system for inspecting and controlling harmful substances includes probe assemblies that each includes a sensor comprising nano structured surfaces or nano particles in a solution, configured to adsorb molecules of a sample material captured adjacent to the sensor, a laser that can emit a laser beam to illuminate the molecules adsorbed to the nano structured surfaces, a spectrometer that can produce spectral data from light scattered by the molecules adsorbed to the nano structured surfaces, and a ID reader that can retrieve identification information about the sample material. A central office can determine a spectral signature matching spectral signatures stored in a database and to identify a harmful substance in the sample material. An alert and response system can send out an alert signal about the sample material when the harmful substance is identified in the sample material.

30 Claims, 31 Drawing Sheets

MONITORING NETWORK BASED ON NANO-STRUCTURED SENSING DEVICES

CROSS-REFERENCE TO RELATED APPLICATIONS

The present application is a continuation-in-part application of and claims priority to commonly assigned U.S. patent application Ser. No. 12/502,903 (issued now as U.S. Pat. No. 7,929,133), filed Jul. 14, 2009, titled "Nano structured sensing device for surface-enhanced Raman scattering", which is a continuation application of and claims priority to U.S. patent application Ser. No. 12/262,667 (issued now as U.S. Pat. No. 7,576,854), filed Oct. 31, 2008, titled "Arrays of nano structures for surface-enhanced Raman scattering", which is a continuation application of and claims priority to U.S. patent application Ser. No. 11/562,409 (issued now as U.S. Pat. No. 7,460,224), filed Nov. 21, 2006. U.S. patent application Ser. No. 11/562,409 further claims priority to U.S. Provisional Patent Application 60/751,472, filed on Dec. 19, 2005. The present application is also a continuation-in-part application of and claims priority to commonly assigned U.S. patent application Ser. No. 12/625,970 (issued now as U.S. Pat. No. 8,213,007), filed Nov. 25, 2009, titled "Spectrally sensing chemical and biological substrates", which is a continuation-in-part application of and claims priority to commonly assigned U.S. patent application Ser. No. 12/403,522 (issued now as U.S. Pat. No. 8,102,525), titled "Systems and methods for detecting chemical and biological substances", filed Mar. 13, 2009. The present application is also a continuation-in-part application of and claims priority to commonly assigned U.S. patent application Ser. No. 12/643,689 (issued now as U.S. Pat. No. 8,081,308), filed Dec. 21, 2009, titled "Detecting chemical and biological impurities by nano-structure based spectral sensing". The disclosures in these related patent applications are incorporated herein by reference.

FIELD OF INVENTION

This invention relates to technologies for monitoring and tracking harmful substances using a network of nano-structured sensors.

BACKGROUND OF INVENTION

Raman scattering is an inelastic scattering of a photon which creates or annihilates an optical phonon. Raman scattering is the result of the interaction of incident photons with chemical molecular vibrations (phonons). A unique chemical molecular structure results in a unique Raman scattering spectrum. Therefore, Raman scattering provides spectral fingerprint details about the chemicals, and can also be used to distinguish molecular isomers and chiral molecules from each other.

Raman spectroscopy became commercially available after invention of lasers in late 1960. A laser beam having a narrow line width is used to illuminate the testing chemicals in solid, liquid or gas forms. The narrow line width of the laser beam can eliminate the overlaps of scattering peaks from photons with various wavelengths. The scattered light is collected by a photon detector such as Charge-Coupled Devices (CCD) or CMOS detector, a Raman spectrum is collected. The Raman shift is defined as the wavelength spacing between the scattering light wavelength and incident light wavelength (laser wavelength). The positions of the peaks correspond to the vibration strengths of various molecular bonds, thus provide a spectral fingerprint of the molecules.

Although Raman scattering is a useful analytical tool, it suffers a major drawback: the scattering signal is very weak due to the very small scattering cross section of molecules. Typically, only about $10^{-8}$ of the incident photons on the chemicals will undergo Raman scattering. Of course, high power laser and high sensitivity CCD detector can be used to improve the scattering signals but coming with the extra costs, additional hardware, and unexpected sample damage. Because of the weak scattering signals, normal Raman scattering application is relatively broad but still very limited.

Surface-enhancement effect by using a roughened surface was found to boost Raman scattering signal. In Surface-Enhanced Raman Spectroscopy (SERS), the sample surface can be formed by deposition of metallic particles or clusters. The surface-enhanced Raman scattering phenomena can be explained by interaction between photons with localized electromagnetic field enhancement and chemical enhancement. The enhancement by SERS has been observed in different research labs. An Intel team used a porous silicon structure with coatings of noble metals such as silver on the surface. The Intel team demonstrated that the enhancement increases as the porous silicon pore-size decreases. All the experiments including the work from Intel can be repeated by another team, but it is difficult to reproducibly demonstrate the same level of enhancement.

Accordingly, there is a need to develop well-controlled nano-surface structures at low cost in order to realize commercialization of SERS for various applications ranging from cargo inspection, food inspection, environment monitoring, disease diagnosis, to forensic and homeland security. There is a need to improve the performance of SERS devices and processing techniques for making the same.

SUMMARY OF THE INVENTION

In one aspect, the present invention relates to a monitoring network system for inspecting and controlling harmful substances which includes a plurality of probe assemblies each comprising a sensor comprising nano structured surfaces or nano particles in a solution, that can adsorb molecules of a sample material captured adjacent to the sensor; a laser that can emit a laser beam to illuminate the molecules adsorbed to the nano structured surfaces; a spectrometer that can produce spectral data from light scattered by the molecules adsorbed to the nano structured surfaces; and a ID reader that can retrieve identification information about the sample material. The monitoring network system includes a central office in communication with the plurality of probe assemblies includes a computer storage that can store one or more spectral signatures each associated with a harmful substance and the identification information for the sample material; a communication device that can receive the spectral data and the identification information from the plurality of probe assemblies; a spectral analyzer that can determine, in the spectral data, a spectral signature matching at least one of the spectral signatures stored in the database thereby to identify, in the sample material, the harmful substance associated with the one of the spectral signatures. The monitoring network system includes an alert and response system in communication with the spectral analyzer, wherein the alert and response system can send out an alert signal about the sample material when the harmful substance is identified in the sample material.

Implementations of the system may include one or more of the following. The identification information can include a product name and/or model number, a batch number, a location where the sample material is collected, the source of the sample manufactures or deliverers, the vehicle license number, the distribution channels, and destination of the sample material, and above listed information about detected harmful substances. The central office can further include a controller that can calculate a location the sample material at a specific a time using the spectral data obtained from two or more of the plurality of probe assemblies and using the locations of the two or more of the plurality of probe assemblies. The plurality of probe assemblies can be installed in or around a building, an airport, a custom, a conveyance system for cargo or luggage, a doctor or a health advisor's office, a check station on a road, a harbor, in a vehicle, a ship, a submarine, an airplane, a train, a subway, an industrial site, a resort area, a shopping mall, a research Lab, a school, a shopping mall, a water source, or a people gathering place. The spectral data can include a Raman spectrum. The nano structured surfaces in the sensor can include three dimensional structures each having a width between about 1 nm and about 300 nm. The plurality of nano structures can include at least one of recesses, nano rods, or nano holes. Adjacent nano structures can have spacing between about 1 nm and about 1000 nm. The nano structures can have heights between about 1 nm and about 1000 nm. The sensor can include a substrate and wherein the nano structured surfaces comprise nano particles introduced on the substrate. The nano structured surfaces in the sensor can include: an active material having active nano surfaces; and an inactive material having inactive nano surfaces in proximity to the active nano surfaces, wherein the active nano surfaces have widths between about 1 nm and about 300 nm. The sensor can include a substrate comprising the inactive material and a first layer comprising an active material over the substrate, wherein the first layer includes a plurality of recesses that expose the substrate. The active material can include a metallic material. The active material can be selected from a group consisting of Ag, Au, Cu, Pt Al, Fe, Co, Ni, Ru, Rh, and Pd. The inactive material can include an insulator. The inactive material can be selected from a group consisting of silicon dioxide, aluminum oxide, silicon nitride, tantalum oxide, and titanium oxide. The sensor further can include an adsorption layer on the first layer. The adsorption layer can include a material selected from a group consisting of $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, a metal doped with chlorine or chloride, and a polymeric material. The sample material can be extracted from a food product. The harmful substance can include melamine, sodium cyclamate, sodium cyclohexylsulfamate, cane sugar, starch, nitrite, nitrate, sulfide, Sudan I, II, III and IV, malachite green, methomidophos, acephate, DDT, DDV, malathion, fenitrothion, malathion, malathion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methyl parathion, phosmet, dimethoate, nitrofuran, furanzolidole, chloramphenicol, chlortetracycline, ciprofloxacin, clenbuterol, ractopamine, enorfloxacin, rhodanmine B, benzoic acid, hyposulfurous acid, sodium formaldehyde, formaldehyde, phthalates, dioxins, Pd, Cd Hg, As, and Cr in water, cyanides, chlorates, sulfates, crysoidine G, boric acid and borax, sodium sulfocyanate, lead chrome green, Basic Flavine O, industrial used formaldehyde and NaOH, carbon monoxide, sodium sulfate, industrial surfer, industrial dyes, fructus papaveris, over dosed level of food colorants, food preservants, sweeteners, emulsifier, swelling agents overdose, bleach, sulfer suffumigation, color protectants, $TiO_2$, benzoyl peroxide, olaquindox, chloromycetin, or $KAlSO_4$. The harmful substance can include an explosive material, a flammable material, a narcotic drug, a poisonous gas, a radioactive material, or contagious virus and bacteria. The sample material can include a body fluid obtained from a person or an animal, wherein the one or more spectral signatures are associated with a disease or an illicit drug use in the person or an animal based on the spectral signature. The central office further can include a qualification system that can qualify the sample material, wherein the database is configured to store the qualification status in association with the identification information. The ID reader in at least one of the plurality of probe assemblies can include an RFID reading device, a mobile phone, a camera phone, a barcode reader, and a computing input device. The computer storage can store a high-risk target list of entities that produce, transport, distribute, or sell the harmful substance identified in the sample material to allow the plurality of probe assemblies to more frequently track and monitor these entities.

In another aspect, the present invention relates to a monitoring network system for inspecting and controlling harmful substances including a plurality of probe assemblies that each comprising: a sensor comprising nano structured surfaces or nano particles in a solution, that can adsorb molecules of a sample material captured adjacent to the sensor; a laser that can emit a laser beam to illuminate the molecules adsorbed to the nano structured surfaces; a spectrometer that can obtain spectral data from light scattered by the molecules adsorbed to the nano structured surfaces; and a ID reader that can retrieve identification information about the sample material. The monitoring network system also includes a plurality of central offices that are connected in a computer network, wherein each of the central offices comprises: a computer storage that can store one or more spectral signatures each associated with a harmful substance and the identification information for the sample material; a communication device that can receive the spectral data and the identification information from one or more of the plurality of probe assemblies; and a spectral analyzer that can determine, in the spectral data, a spectral signature matching at least one of the spectral signatures stored in the computer storage thereby to identify, in the sample material, the harmful substance associated with the one of the spectral signatures. The monitoring network system also includes an alert and response system in communication with the plurality of central offices, wherein the alert and response system is configured to send out an alert signal about the sample material when the harmful substance is identified in the sample material in one or more of the plurality of central offices.

The present invention provides a novel surface device comprising a substrate supporting a plurality of nano structures and an exposed sensing surface upon the nano structures, wherein said surface includes at least one active SERS nano surface and at least one inactive SERS nano surface established in proximity to the active SERS nano surface.

An array of the nano-structures is provided to enhance the chemical adsorption to the array surfaces, thus further improve the SERS sensitivity. In one embodiment, the charge states of the measured chemicals are utilized. Electrical bias can be applied to the nano-structures or to a function layer built under the nano-structure surface to attract the chemicals to the array surface. The bias can be varied from negative to positive based on chemical properties of the measured chemicals by SERS. In another embodiment, a thin chemical function layer with special surface bonds to attract the measured chemicals is constructed. In another embodiment, cooling the whole array structure with the substrate to a specific temperature is designed to selectively condense the measured chemicals to the array surface. In another embodiment, a magnetic field is applied to the sensing surface, or function layer at the sensing surface containing magnetic materials, such as Fe, Co, Ni, or their compounds. In this way, the chemical polar molecules on the sensing surface are aligned to a preferred orientation. The applied magnetic field or localized magnetic materials in the active layer can enhance chemical specific binding and enhance molecule surface binding efficiency, resulting enhanced Raman signal.

The present invention also provides a method of forming a surface sensing device comprising: providing a substrate, depositing at least one layer of material upon the substrate, establishing a pattern upon the layer of material, the pattern defining a plurality of nano structures, removing a portion of the layer of material to define side walls of the nano structure, and forming an exposed sensing surface upon the nano structures, wherein said surface includes at least one active SERS nano surface and at least one inactive SERS nano surface established in proximity to the active SERS nano surface.

The nano structures can be formed on a substrate such as silicon, GaAs, ZnS, CdSe, sapphire, $Al_2O_3$, glass, Ti, Ni, Cr, Al, and Cu. The dimensions of the nano structures can be between 1 nm to 300 nm, preferably 5 nm to 50 nm, with a spacing of 1 nm to 1000 nm, preferably 5 nm to 50 nm between the structures. The nano structures can have depths or heights between 1 nm to 1000 nm. The surface function layer thickness can be between 0.5 nm-500 nm. The bias layer thickness can be between 50 nm to 10 µm. The shape of the nano structures have a geometry selected from at least one of circular, triangle, quasi-triangle, square, rectangular, hexagonal, oval, elliptical, rectangular with a semi-circles or triangles with rounded corner at both ends alone either long or short axis, and rectangular with four rounded corners. These nano-structures could be either isolated islands or connected one another.

Materials suitable for the surface functional layer or thermal bias layer can include noble metal and transition metal such as Ag, Au, Cu, Al, Fe, Co, Ni, Ru, Rh, Pd, and Pt for nano structure substrate. Materials suitable for the surface function layer can include Ag oxide, Au oxide, $SiO_2$, $Al_2O_3$, $Si_3N_4$, $Ta_2O_5$, $TiO_2$, ZnO, $ZrO_2$, $HfO_2$, $Y_2O_3$, Tin oxide, antimony oxide, and other oxides; Ag doped with chlorine or chloride, Au doped chlorine or chloride, Ethylene and Chlorotrifluoroethylene (ECTFE), Poly(ethylene-co-butyl acrylate-co-carbon monoxide) (PEBA), Poly(allylamine hydrochloride) (PAH), Polystyrene sulfonate (PSS), Polytetrafluoroethylene (PTFE), Polyvinyl alcohol (PVA), Polyvinyl chloride (PVC), Polyvinyldene fluoride (PVDF), Polyvinylprorolidone (PVP), and other polymers; stacked multiple layers at least two layers including above listed metal layers and non-metal layers, etc. The thermal bias layer can be electrically isolated or connected to the array. A typical material is a metal such as Ti, Ni, Cr, Pt, Ru, Ni—Cr alloy, NiCrN, Pt—Rh alloy, Cu—Au—Co alloy, Ir—Rh alloy or/and W—Re alloy.

The present invention provides a trace chemical substance detection system. The system comprises a spectroscopy system operatively associated with a surface device comprising: a substrate supporting a plurality of nano structures, an exposed sensing surface upon the nano structures, wherein said surface includes at least one active SERS nano surface and at least one inactive SERS nano surface established in proximity to the active SERS nano SERS surface. In one embodiment, the spectroscopy system comprises a laser beam source generating a laser beam, an optical assembly focusing the laser beam, an deflection system directing the laser beam at an array device, a collector receiving a portion of said laser beam scattered by said array device; and an spectrum analyzer receiving said portion and generating an output indicative of the composition and or concentration of chemicals on the array device.

The array of nano surface structure can be used for SERS applications for liquid and gas phase measurements of trace chemical detections. It can be also applied the array to other spectroscopy measurements including surface-enhanced Raman resonance spectroscopy (SERRS), surface-enhanced coherent-anti stokes Raman scattering (SECARS), surface-enhanced infrared absorption (SEIRA) spectroscopy, surface-enhanced fluorescence spectroscopy, surface-enhanced photoluminescence spectroscopy, time-resolved measurements with above techniques, and combination of above techniques for chemical fingerprint identification and trace chemical sensing.

The present invention provides an in-situ cleaning method. Thermal-electrical heating is applied to the bias metallic layer to heat array of the nano surface structure up to 500° C. Many adsorbed chemical molecules and unexpected surface contamination will be physically evaporated or even burn out at the high temperature, resulting in a clean array to prevent cross contamination of previous measurements, and reuse of the array for SERS.

In another aspect of the present invention, a method for detecting molecules includes a) introducing a trace amount of chemical onto an array device allowing molecules of the chemical being adsorbed onto an sensing surface of the array device, b) irradiating the array device with a laser beam, c) collecting scattered photons from the adsorbed molecules, and d) detecting Raman spectrum from the scattered photons. The array device can include a substrate supporting a plurality of nano structures, the exposed sensing surface upon the nano structures. The surface includes at least one active SERS nano surface and at least one inactive SERS nano surface established in proximity to the active SERS nano surface.

Embodiments may include one or more of the following advantages. The disclosed systems and methods can effectively enhance chemical specific binding, to enhance molecule surface binding efficiency, i.e., to enhance chemical molecule adsorption onto the sensing surface with maximized number of molecules within unit period of time, so that to enhance Raman signal.

DETAILED DESCRIPTION OF THE INVENTION

Figure 1:
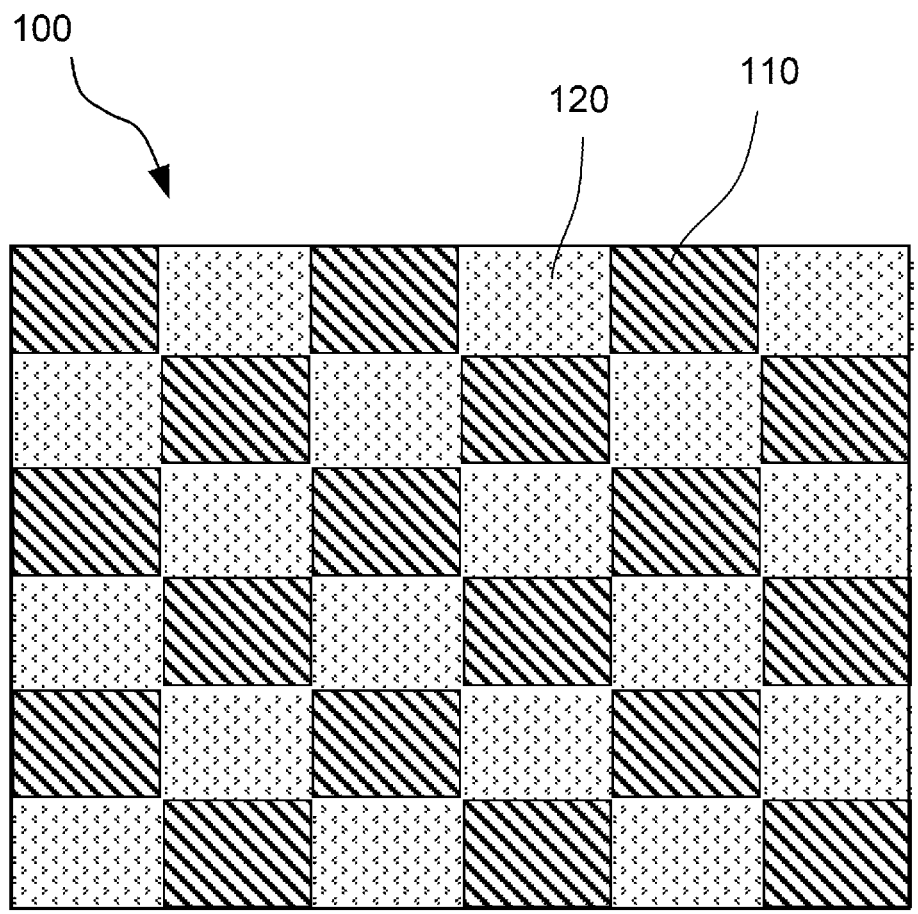
FIG. 1 is a top view of a square array of an array device according to the present invention.

The present invention provides new devices and apparatus/systems as well as methods for improved performance of Surface-Enhanced Raman spectroscopy.

SERS selectivity of surface signal results from the presence of surface enhancement mechanisms demonstrated only at the surface. There are two primary mechanisms of surface enhancement: electromagnetic enhancement and chemical enhancement. The electromagnetic enhancement is dependent on rough features present on the metal surface, while the chemical enhancement involves electronic charge transfer and changes to the adsorbate electronic states due to chemisorption of the analytes.

SERS is observed primarily from analytes adsorbed onto coinage (Au, Ag, and Cu) or alkali (Li, Na, K) metal surfaces, with the excitation wavelength near or in the visible region. Theoretically, any metal would be capable of exhibiting the effect of surface enhancement, but the coinage and alkali metals satisfy calculable requirements and provide the strongest enhancement.

The great part of the overall enhancement of SERS is due to an electromagnetic enhancement mechanism that is a direct consequence of the presence of metal roughness features on the metal surface.

The chemical enhancement mechanism also provides enhancement for the gain of Raman signal intensity. The molecule is adsorbed onto the surface and interacts with the surface. The chemical enhancement exists because of this interaction. The metal adsorbate proximity allows pathways of electronic coupling from which novel charge-transfer intermediates emerge, leading to a SERS condition with higher Raman scattering cross-sections. In addition, the electronic orbits of the adsorbate molecules may contact and interact with the conducting electrons of the metal, altering the chemical state of the chemical substance. It is also proposed that the chemical enhancement may be an alteration in the scattering cross-section, which is the chemical nature of the chemical substance changing due to its interaction with the metal.

The present invention provides an array device comprising a substrate supporting a plurality of nano structures and an exposed sensing surface upon the nano structures, wherein said surface includes at least one active SERS nano surface and at least one inactive SERS nano surface established in proximity to the active SERS nano surface. Accordingly, the performance of this SERS device benefits from both electromagnetic effect and chemical enhancement to the Raman signal intensity.

The term, "active SERS nano surface", when used herein, encompasses a well defined metal surface having at least one surface dimension on a nanometer scale. The surface may or may not be flat. The active SERS nano surface exhibits electromagnetic enhancement to Raman signal under photon irradiation. Examples of materials for the active SERS surface include noble metal such as Ag, Au, Cu, and Pt, and transition metals such as Al, Fe, Co, Ni, Ru, Rh, and Pd. The material used for the active SERS surface is referred as "active material".

The term, "inactive SERS nano surface", refers to a surface having at least one dimension on a nanometer scale. The surface may or may not be flat. In contrary to the active SERS nano surface, the inactive SERS nano surface does not exhibit significant electromagnetic enhancement to Raman signal just by itself. However, when the inactive SERS surface was placed in proximity to the active SERS nano surface, a relatively stronger enhancement of Raman signal was observed, compared with the signal from merely the active SERS nano surface. Therefore, the inactive SERS nano surface arranged in an alternative fashion with the active SERS surface provides further enhancement to Raman signal. Examples of materials for the inactive SERS nano surface include insulators such as $SiO_2$, $Al_2O_3$, $Si_3N_4$, $Ta_2O_5$, $TiO_2$, and air (open space). The material used for the inactive SERS nano surface is referred as "inactive material".

The term, "nano structure", as used herein, is intended to mean a 3-dimensional object either extruded away from the substrate or recessed toward the substrate, having at least one dimension on a nanometer scale. Non-limiting examples of the shape of the nano structure include nano rod, nano pyramid, nano hole, and nano pit.

According to one embodiment of the present invention, an improved SERS performance is achieved by arranging the inactive SERS nano surface next to the nano active SERS surface. FIGS. 1-11 provide exemplary array devices for improved SERS applications.

FIG. 1 is a top view of a square array 100 with a plurality of active SERS nano surfaces 110 and inactive SERS nano surfaces 120 established on a substrate. As shown in FIG. 1, each active SERS nano surface is alternatively arranged with each inactive nano SERS surface. The active SERS surfaces are made from a material selected from a group of noble metals, including but not limited to Ag, Au, Cu and Pt. The active SERS surfaces may also be made from a material selected from a group of transition metals, including but not limited to Al, Fe, Co, Ni, Ru, Rh, and Pd. The inactive SERS nano surfaces are made from insulating materials, including but not limited to $SiO_2$, $Al_2O_3$, $Si_3N_4$, $Ta_2O_5$, $TiO_2$, and open space (air).

Figure 2A:
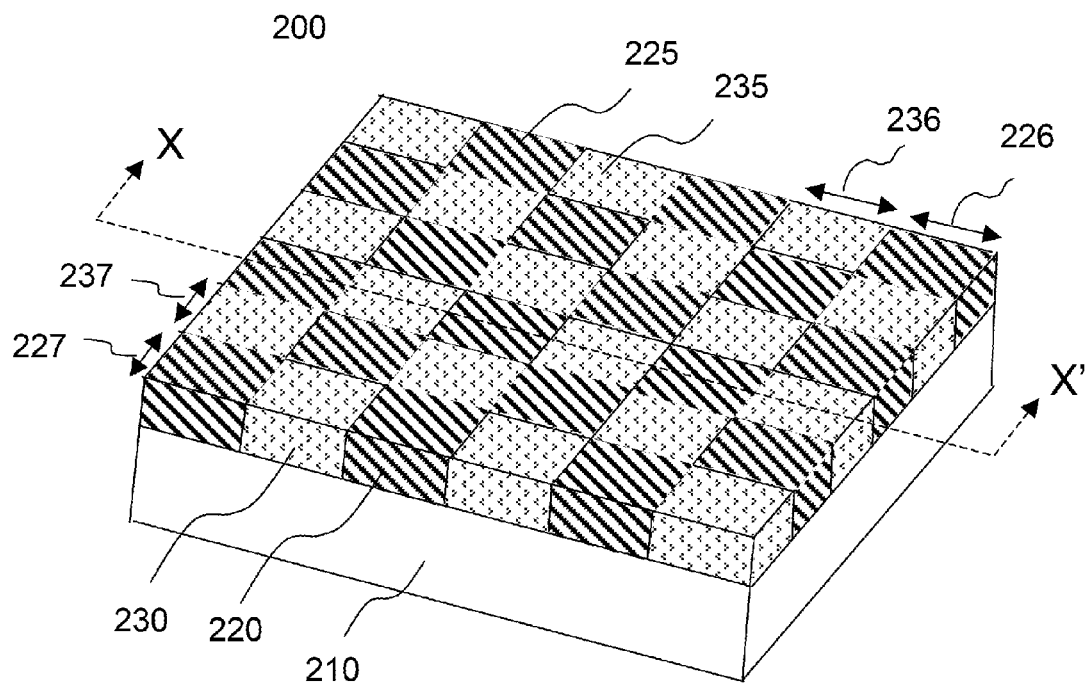
FIGS. 2A and 2B show a square array according to the present invention.

FIG. 2A shows a perspective view of an array device 200 according to one aspect of the present invention. The device comprises a substrate 210, an array of rectangular rods 220 made of an active material and an array of rectangular rods 230 made of an inactive material. Each active rod 220 is alternatively arranged with each inactive rod 230. The active rod 220 provides the active SERS nano surface 225 and the inactive rod 230 provides the inactive nano SERS 235. Both surfaces 225 and 235 are substantially square, having dimensions of 226, 227, 236, and 237 between about 5 nm to 300 nm. In one embodiment, the dimension of the squares is between about 1 nm and about 10 μm.

Figure 2B:
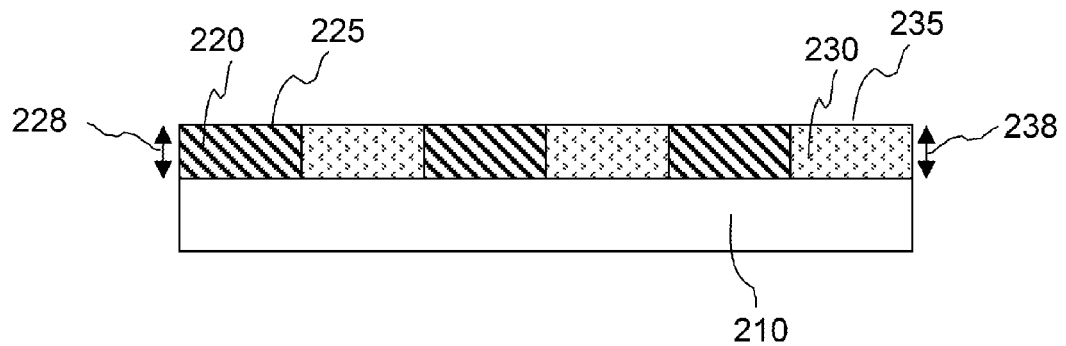

FIG. 2B is a sectional view of the structure of FIG. 2A, sliced at line X-X' of the structure shown in FIG. 1. The height 228 of the active surface 225 is substantially equal to the height 238 of the inactive surface 235. The height 228 and 238 is between 5 nm to 1000 nm. In one embodiment, the height 228 and 238 is between 1 nm to 5 μm.

Figure 3A:
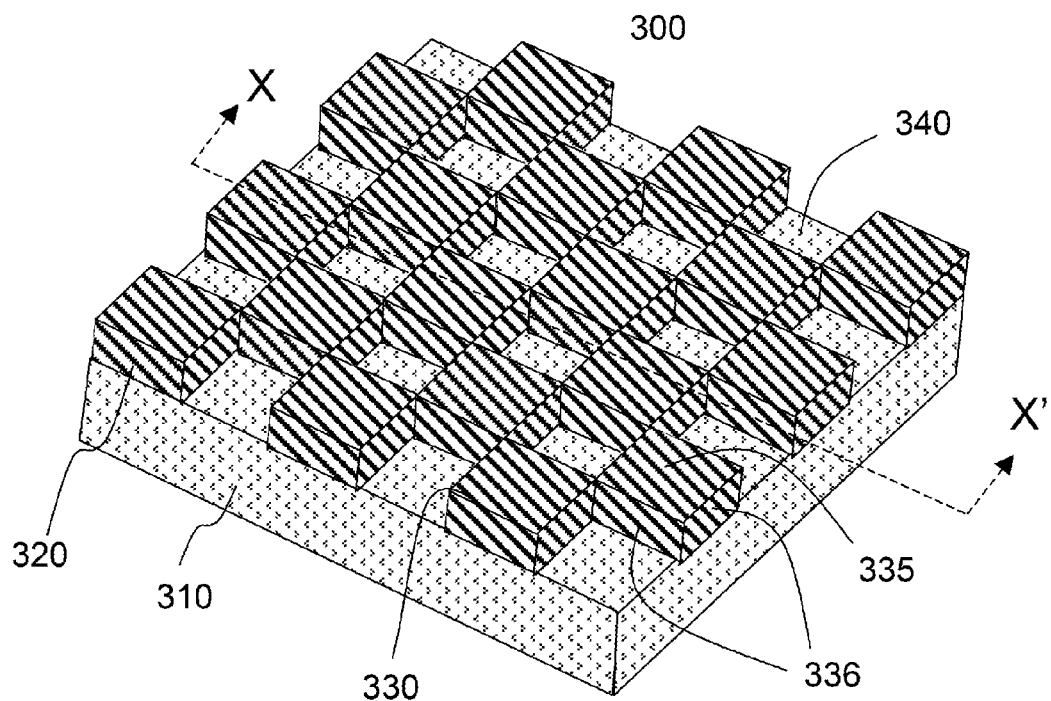
FIGS. 3A and 3B show a square array according to the present invention.
Figure 3B:
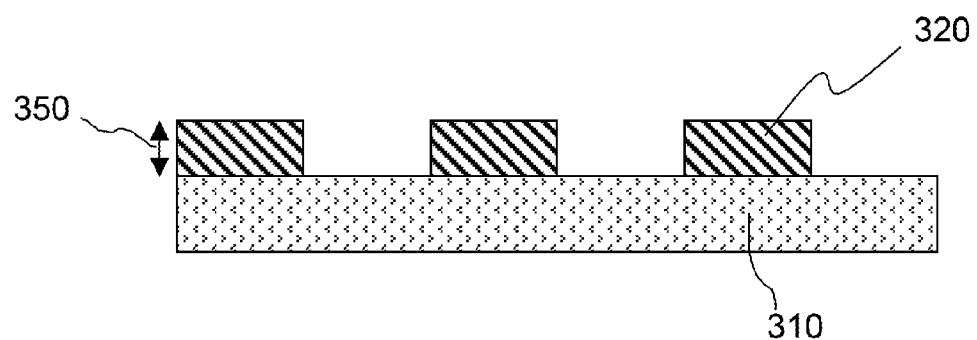

FIG. 3A shows a perspective view of another square array 300. The substrate 310 is made from an inactive material. A plurality of square rods 320 are formed on the substrate. The rod 320 provides the active SERS nano surface 330, which includes top surface 335 and side wall 336. The active SERS nano surface 330 is surrounded by four square areas 340 of inactive SERS nano surfaces. The square area 335 of the active SERS surface is substantially equal to the inactive area 340. A sectional view of a cutoff at line X-X' is shown in FIG. 3B. The height 350 of the rod 320 is between 5 nm to 1000 nm. In one embodiment, the height 350 of the rod 320 is between 1 nm to 5 μm.

The detection sensitivity of the Raman scattering sensors can be enhanced when at least a portion of the nano structures or nano surfaces (active or inactive) has a nano feature size functionally matched with a characteristic parameter of electrons or phonons such as an electron mean-free path (MFP) of electrons on the surface, electron wavelength of electrons on the surface, a phonon MFP of phonons on the surface and a phonon wavelength of phonons on the surface.

The term "nano feature size" is used herein to refer to the dimensions of an active nano SERS surface such as the diameter of an active nano SERS surface, the height or depth of a nano rod or a nano hole, or the spacing between nano structures in the array device.

The term, "functionally match" as described above may include the condition that the nano feature size is approximately equal to, smaller than, integer numbers of, or with a special mathematical function to the characteristic parameter of electrons or phonons.

Figure 4:
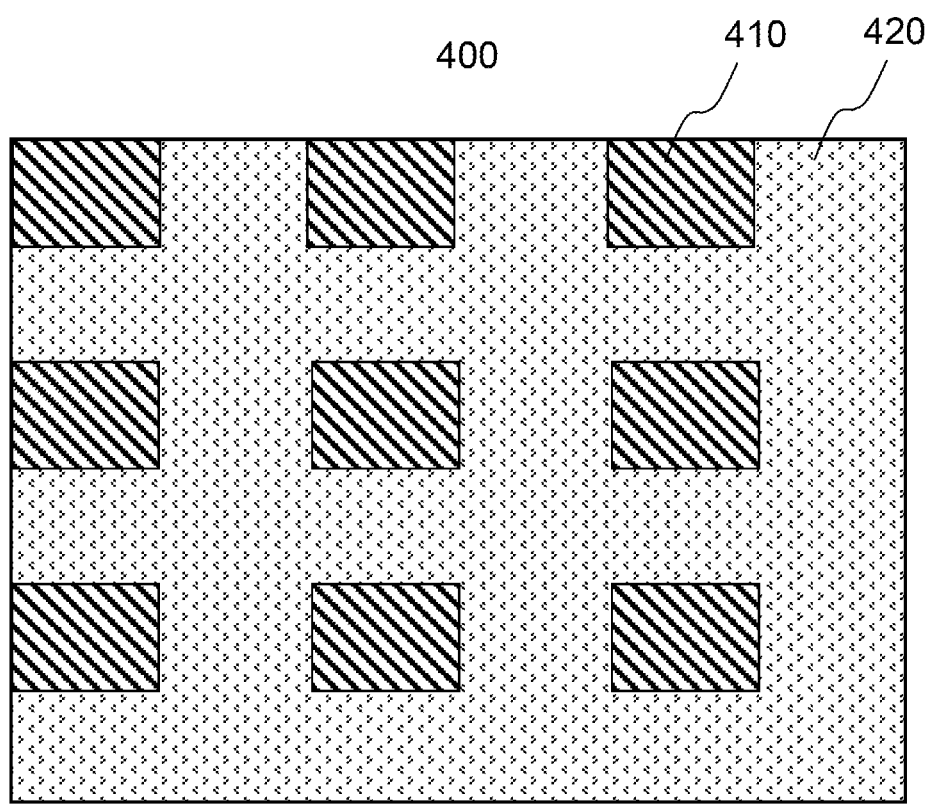
FIG. 4 is a top view of another square array according to the present invention.

FIG. 4 shows another example of a square array 400 of nano surface structure where the active SERS surfaces 410 are physically isolated from each other by inactive SERS nano surface 420. Again, the spacing between the active areas can be air or insulating materials as illustrated in FIGS. 2 and 3.

Figure 5A:
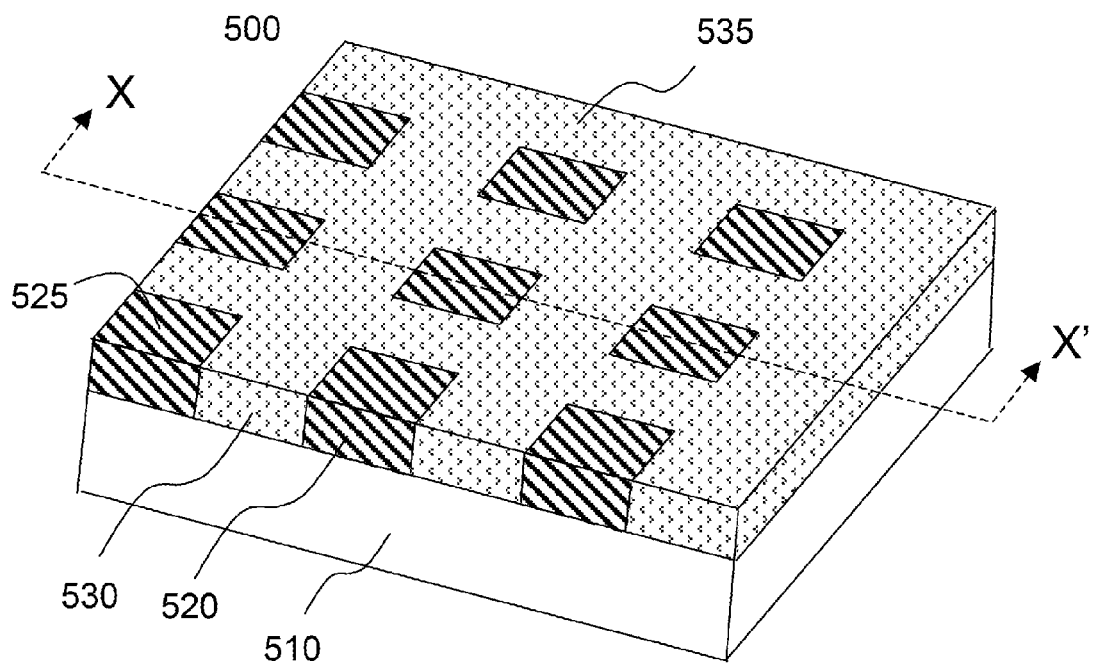
FIGS. 5A and 5B show a square array with isolated active areas and surrounding inactive areas.
Figure 5B:
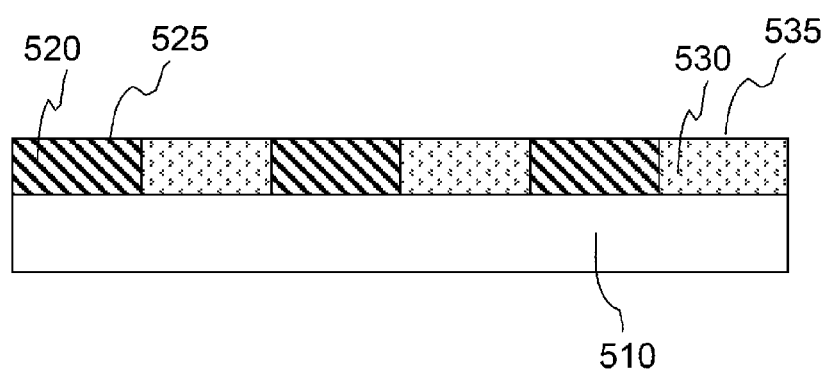

Referring now to FIGS. 5A and 5B, an array device 500 having square rods 520 of an active material is established on a substrate 510. Each rod 520 is surrounded by a region 530 made of an inactive material. A cutoff view from line X-X' is shown in FIG. 5B. Each active SERS nano surface 525 is isolated by an inactive nano surface 535.

Figure 6A:
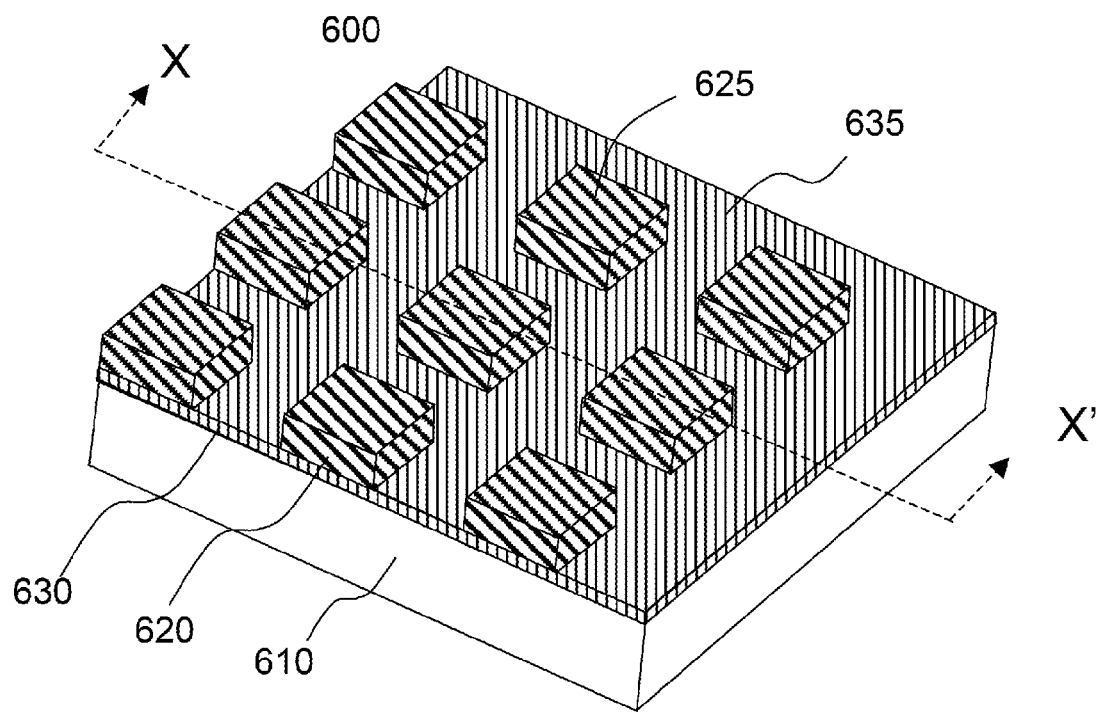
FIGS. 6A and 6B show a square array with a layer of active material connecting each of the active nano surface structure.
Figure 6B:
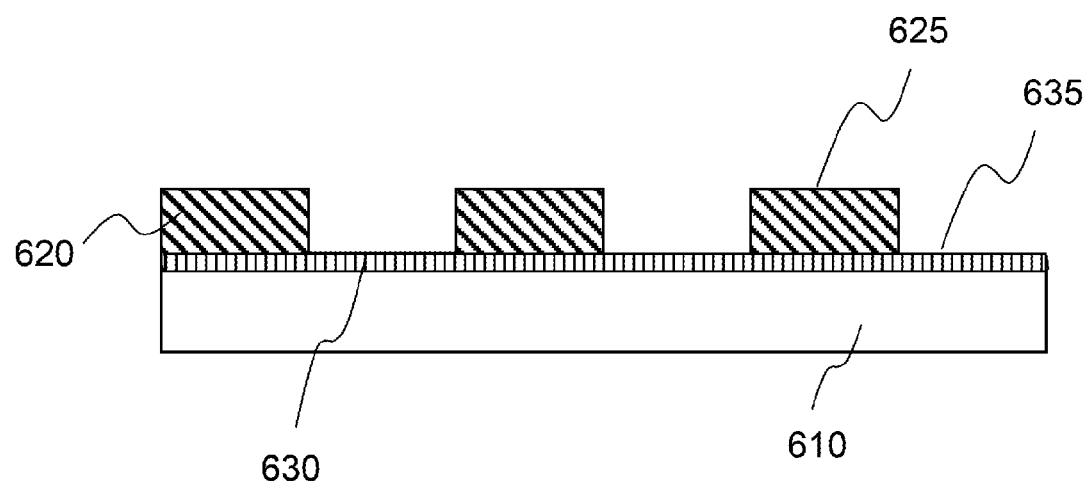

In some embodiments, FIG. 6A is a perspective view showing an array device 600 having a substrate 610 covered by a layer 630 of an active material. Square rods 620 of another active material established on the layer 630. A cutoff view from line X-X' is shown in FIG. 6B. Each active SERS nano surface 625 is isolated by another active nano surface 635. In a special case, a same active material is used for both square rods 620 and layer 630 and the active structures are connected at the bottom of the active areas. The connecting materials can be same as in the active area or different conductors.

Figure 7:
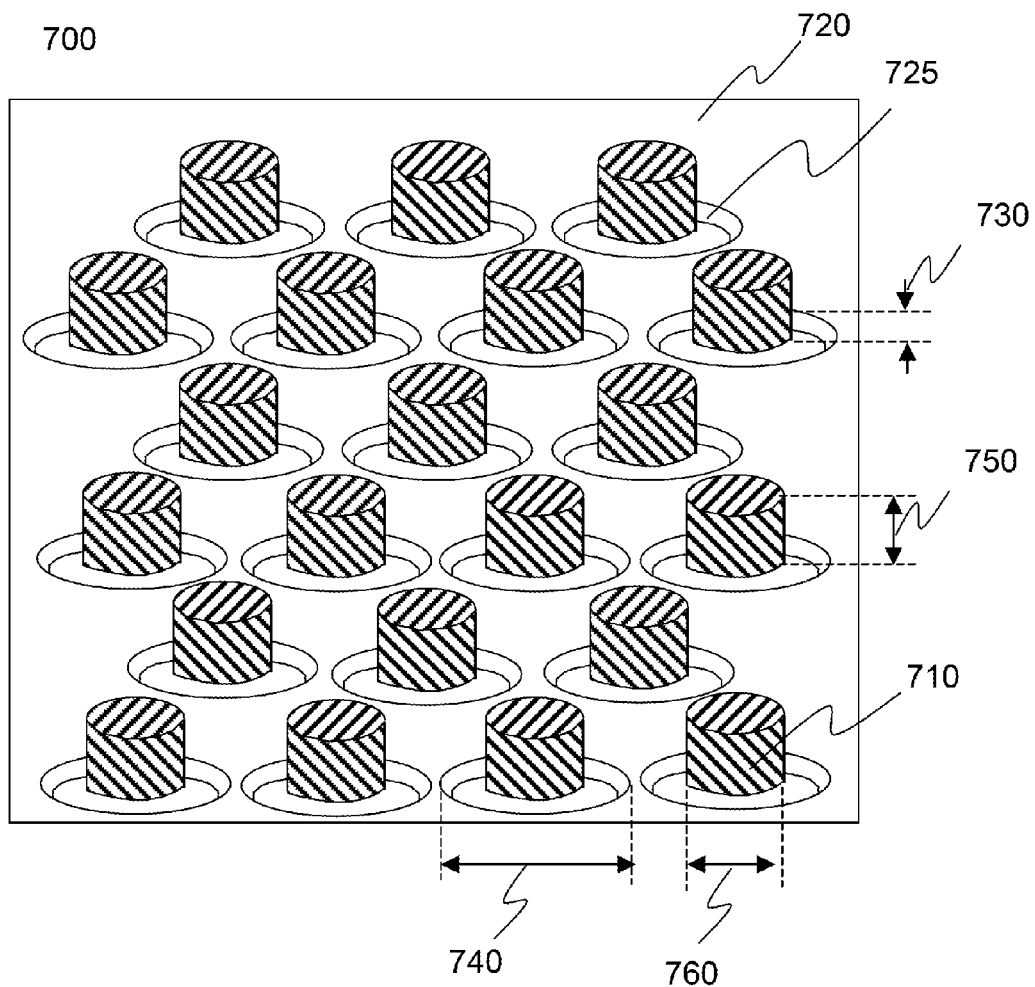
FIG. 7 is a three dimensional view of cylindrical form of array of independent active nano surface structures on surrounding inactive area, with an inactive area depression at the bottom of each of the active nano surface structures.

It is to be understood that the shapes of the nano structures can be altered as desired for specific applications. FIGS. 7-9E show examples of nano rods or nano holes. FIG. 7 shows a perspective view of cylindrical form of array of nano surface structures 700. The independent active areas in their cylindrical forms 710 are regularly distributed on surrounding inactive area 720 to form an array of the nano surface structures 700. The bottom of each of the active cylinder is situated on a depression 725 in the inactive area 720. The depth 730 of the depression in the inactive area is smaller than the height 750 of the cylindrical active rod 710. The diameter 740 of the depression 725 is larger than the diameter 760 of the active rod by a distance on a nanometer scale. Various geometrical features can be designated to maximize the adsorption of molecules. The depression shown on this figure is one of the examples of the enhancement providing structure.

Figure 8A:
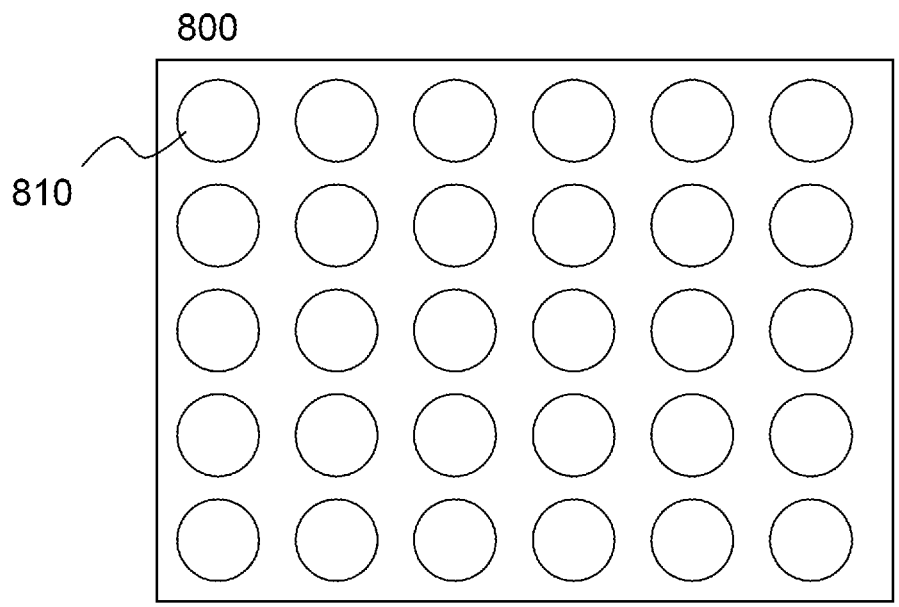
FIGS. 8A and 8B are top views of circular arrays.
Figure 8B:
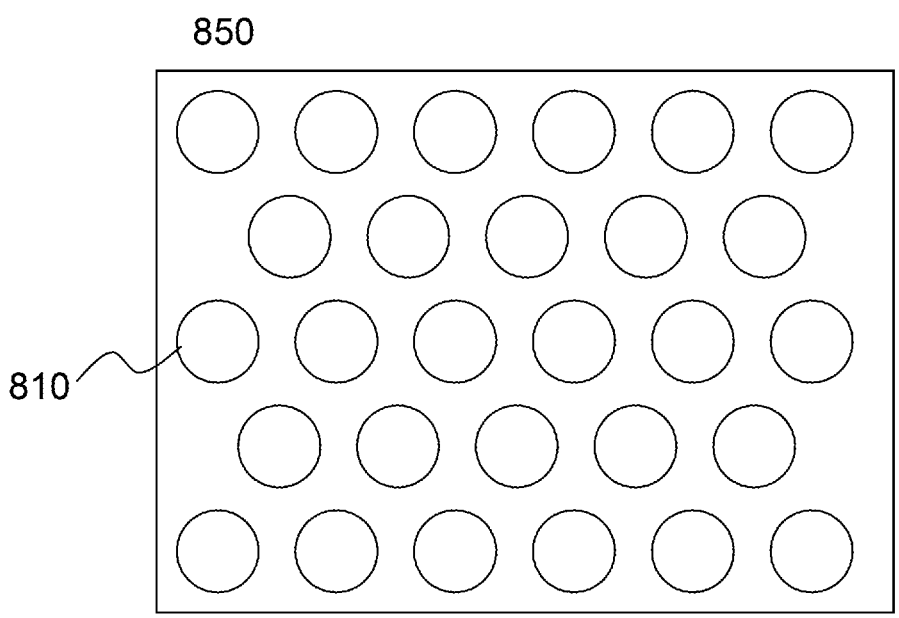

FIG. 8A shows a top view of circular array 800 of nano surface structures which are regularly distributed on a substrate. The area in circles 810 can be the active SERS nano surface or the inactive SERS nano surface (or even air, meaning empty). FIG. 8B shows a top view of another circular array 850 of nano surface structure with a tight packaging of the circles on a substrate.

Figure 9A:
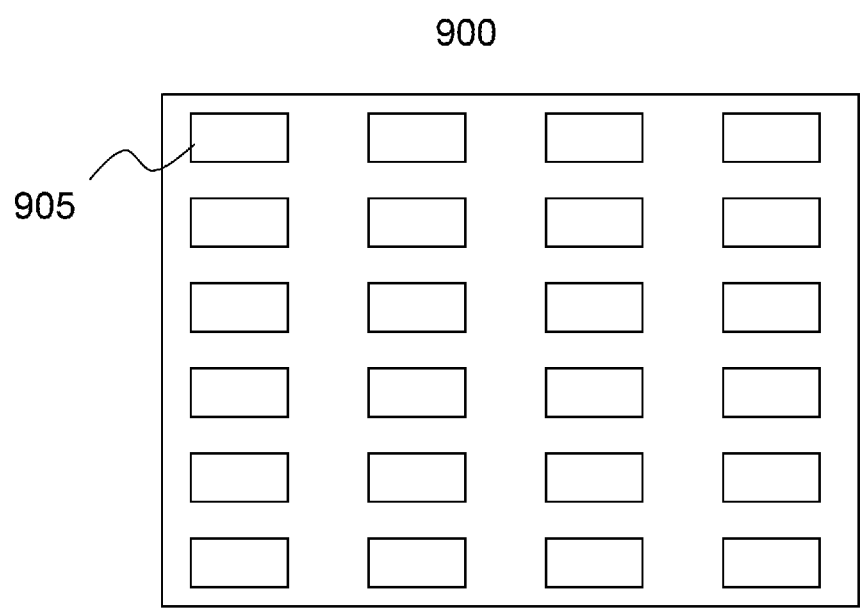
FIGS. 9A-9E show top views of arrays of various shapes.
Figure 9B:
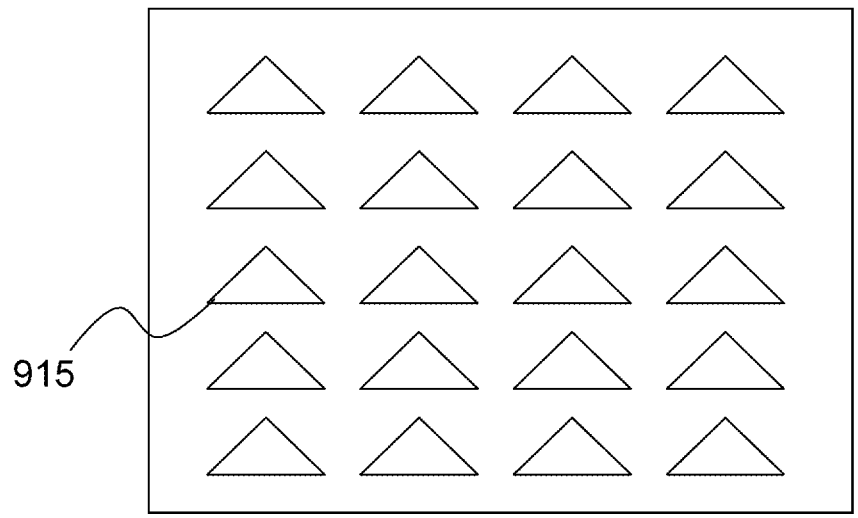
Figure 9C:
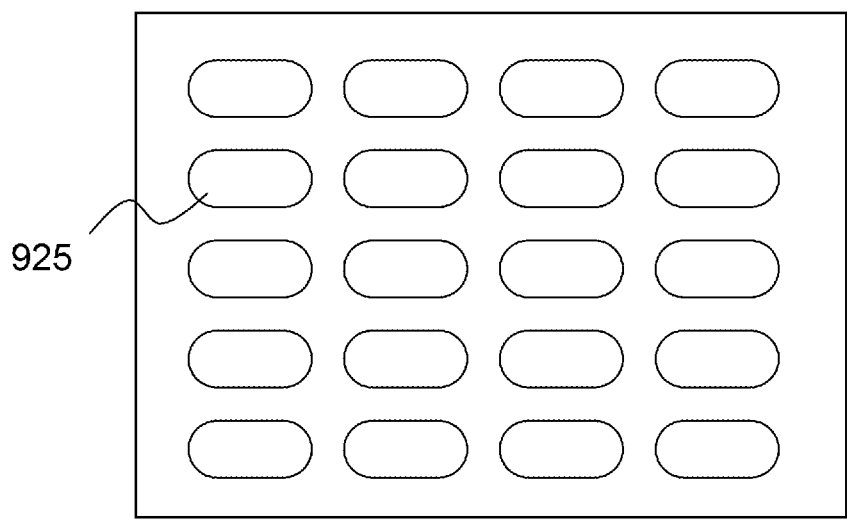
Figure 9D:
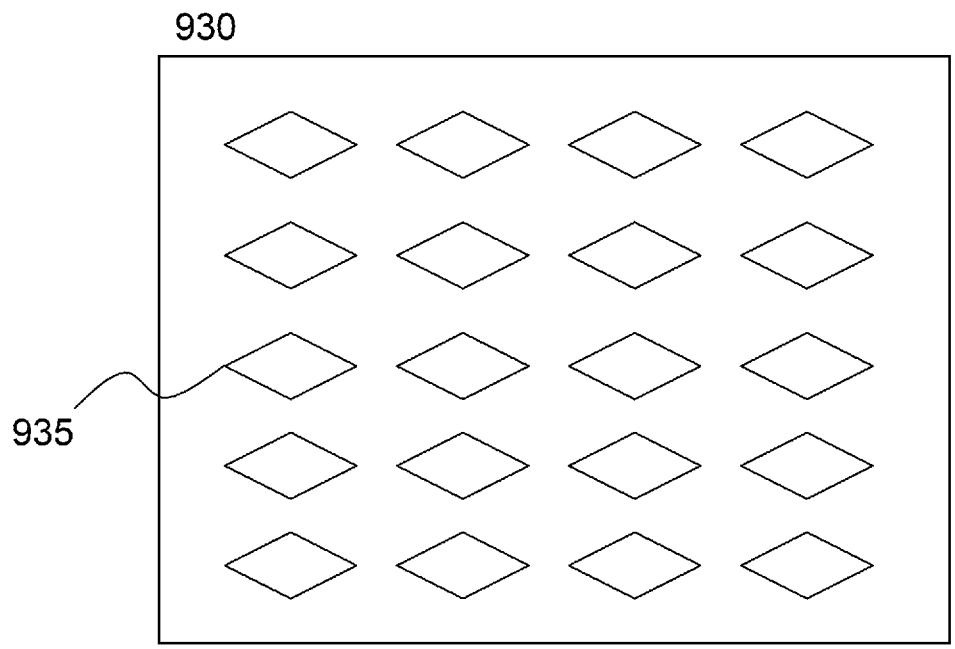
Figure 9E:
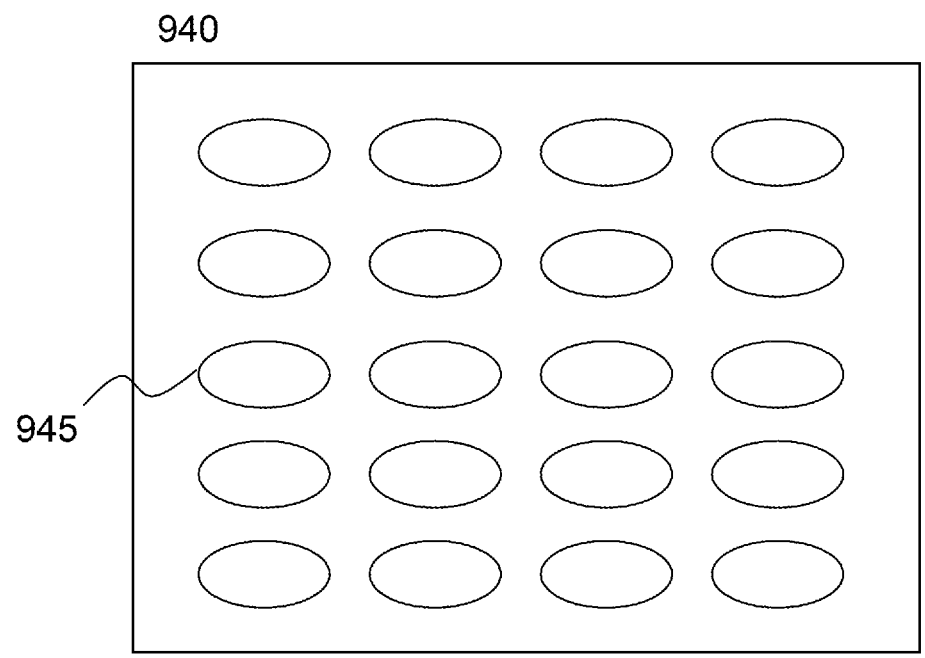

FIG. 9A shows a top view of an array 900 of rectangular nano surface structures 905. FIGS. 9B-9E show a top view of arrays 910, 920, 930, and 940 of triangular 915, round rectangular 925, diamond 935, and oval 945 shapes of nano rods or nano holes.

Figure 10:
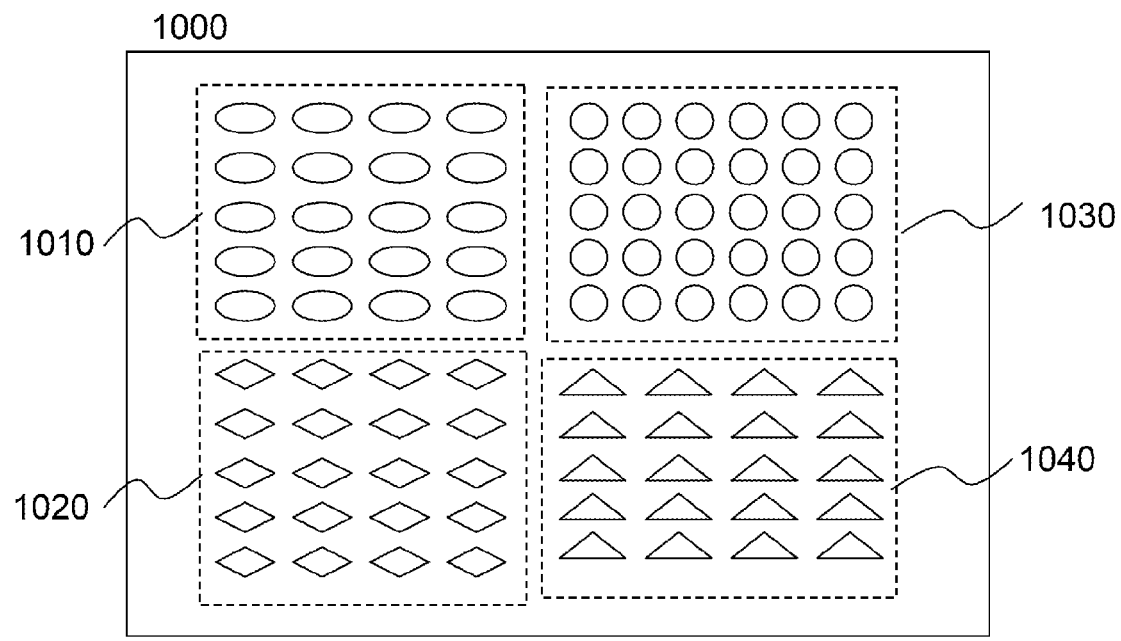
FIG. 10 shows an array comprising sub-arrays with various shapes.
Figure 11:
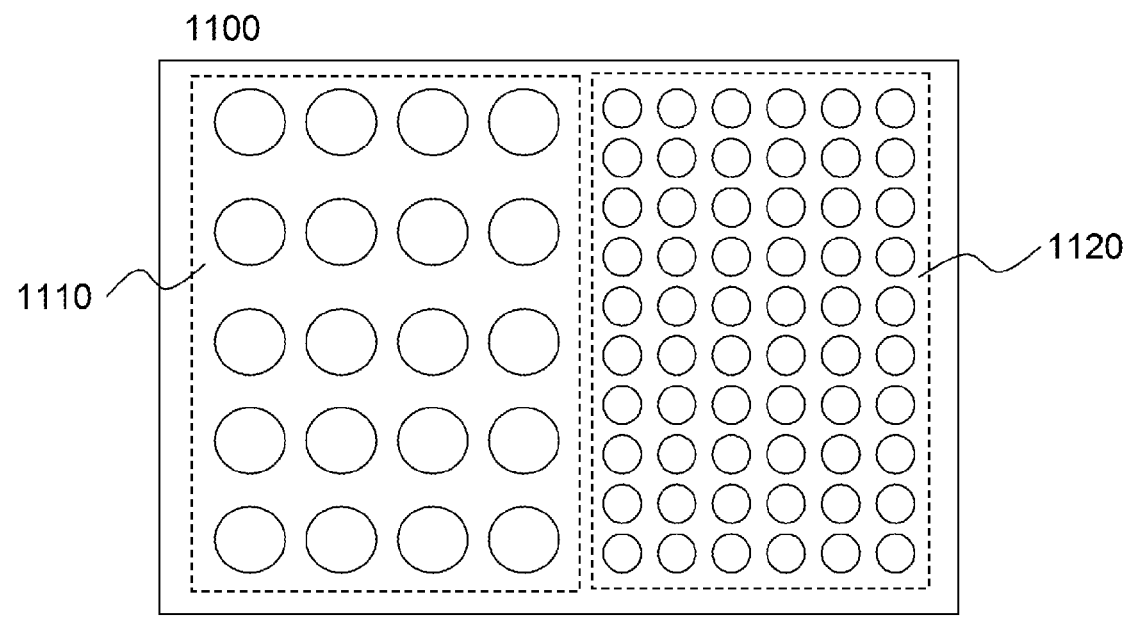
FIG. 11 shows an array comprising sub-arrays with various sizes.

FIGS. 10 and 11 illustrate that an array device can include a number of sub arrays on a substrate. An advantage of the combination of the sub-arrays is that the nano surface structures are optimized for chemical measurement by SERS for a wide range of substances. The combination of different arrays can be used as a general Raman enhancement tool.

FIG. 10 shows a top view of an array device 1000 having sub-arrays 1010, 1020, 1030, and 1040. Each of the sub-arrays has different shapes of the nano structures. FIG. 11 illustrate an array device 1100 having sub-arrays 1110 and 1120. The sub-arrays may have the same shape but have different size.

Figure 12:
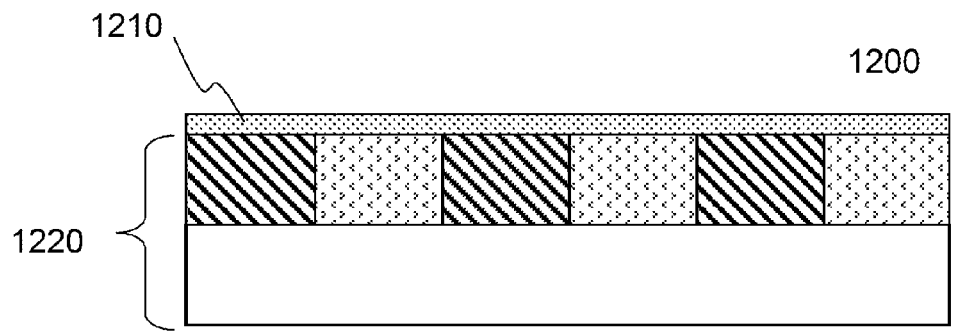
FIG. 12 is a cross sectional view of an array with a surface adsorption layer over the entire array.

With reference now to FIG. 12, an array device 1200 which has an adsorption layer 1210 over a structure 1220 which is similar to array 200 or 500 shown in FIG. 2 and FIG. 5 respectively. Based on the specific chemical bonding configurations of a measured chemical in SERS, the surface adsorption layer 1210 can be selected with adequate chemical bonds, either positive charged or negative charged, so that the measured chemicals can be adsorbed to the surface, and moved to close to and then adsorbed onto the active areas. The adsorption layer does not need to be very thick. In some cases, a monolayer or even island distributed layer will be sufficient. The layer thickness can be between 0.5 nm and 500 nm, preferred between 2 nm-20 nm. Material suitable for the adsorption layer can include Ag oxide, Au mixed with oxide, $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, or other metal oxide layer, metal layer doped with chlorine or chloride, polymers, etc.

Figure 13:
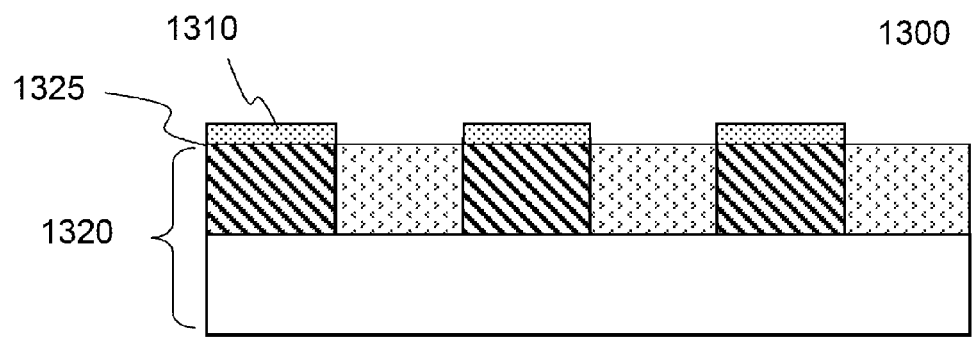
FIG. 13 is a cross sectional view of an array with a surface adsorption layer selectively covering active SERS nano surfaces.
Figure 14:
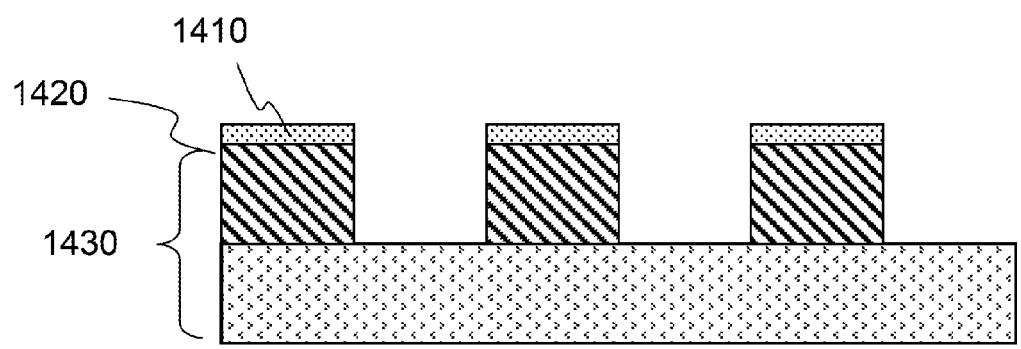
FIG. 14 is a cross sectional view of an array with a surface adsorption layer selectively covering active SERS nano surfaces according to the present invention.
Figure 15:
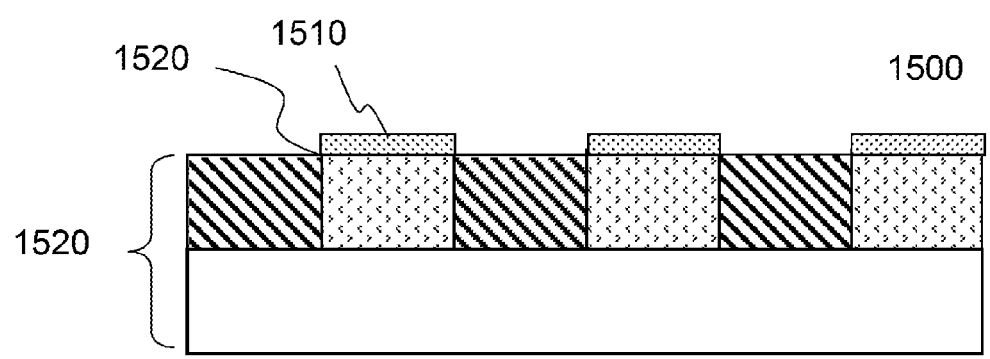
FIG. 15 is a cross sectional view of an array with a surface adsorption layer selectively covering inactive SERS nano surfaces.

FIGS. 13-15 illustrate various arrangements of the adsorption layer over an array device. In one embodiment, the adhesion layer covers only the active SERS nano surfaces. FIG. 13 shows an array device 1300 having the adsorption layer 1310 disposed selectively on the inactive SERS nano surfaces 1325. The structure 1320 is similar to the array device 200 or 500 shown in FIGS. 2 and 5 respectively. Alternatively, an adsorption layer 1410 may be selectively disposed on the active SERS nano surface 1420 for array 1400 shown in FIG. 14.

In another embodiment, an adsorption layer 1510 may be selectively disposed on top portion of the isolated inactive SERS nano surface 1520 as shown in FIG. 15. The structure 1530 is similar to array structure 300 shown in FIG. 3.

The presently disclosed device is compatible with other arrangements of the adsorption layer, which can help bring molecules of an analysis close enough to the active nano SERS surface.

Figure 16:
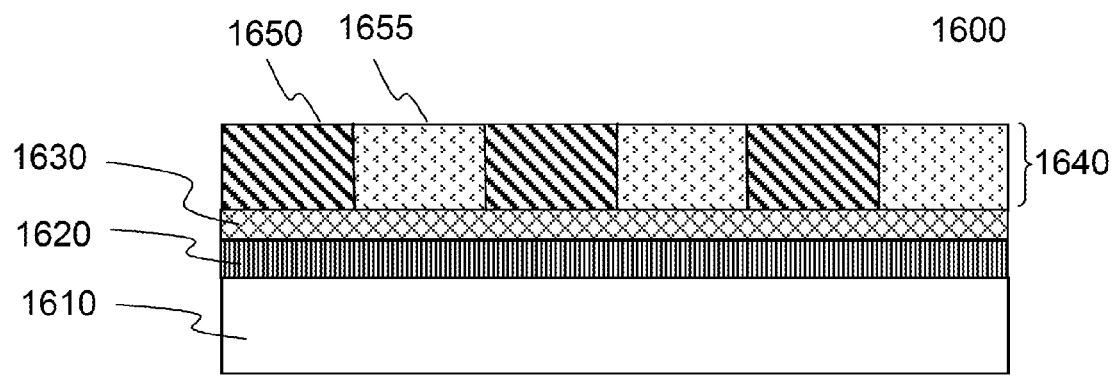
FIG. 16 is a cross sectional view of an array device with a function layer between a substrate and an array of nano structures.

In some embodiments, an enhancement of molecule adsorption to the device surface is provided by electrical biasing. FIG. 16 shows a device 1600 of an array of nano surface structure 1640 with active and inactive SERS nano surfaces 1650 and 1655 over a metallic layer 1620 on a substrate 1610. There is an optional insulator layer 1630 separating the array 1640 from the metallic layer 1620. Based on the charge states of the measured chemical molecules, a positive or negative bias can be applied to the metallic layer 1620 to attract the molecules to the sensing surface 1650 and 1655.

The metallic layer 1620 is also referred as a function layer. The term, "function layer", as used herein, refers to a layer providing electrical, magnetic, or thermal bias to the array device of nano surface structure.

Figure 17:
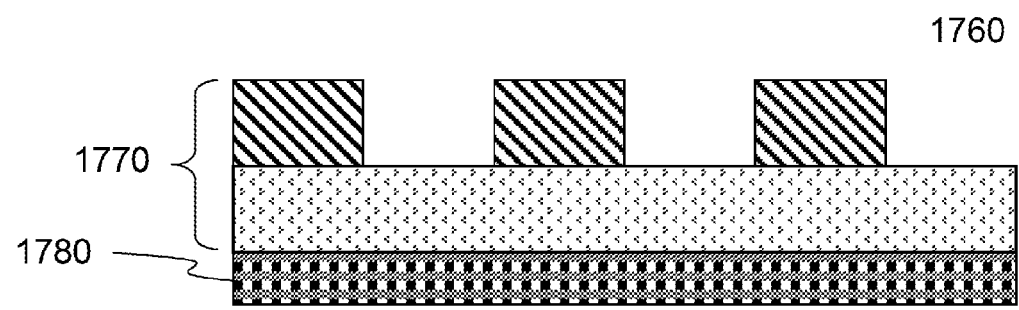
FIG. 17 shows another array device with a function layer.

In some embodiments, molecular adsorption to the device surface can be enhanced by lowering the temperate of the whole array. Giving the array is much thinner than the substrate, a thermal electrical cooler can be connected to the bottom of the substrate, or to the metal pad area of a sensing chip. Referring to FIG. 17, an array device 1760 includes a thermally conductive substrate 1780. By applying an electrical field to a cooler, the substrate 1780 including the nano array 1770 can be cooled down to, for example, a temperate range from −20° C. to 20° C. A lower temperature can be achieved by using a more expensive thermal electrical or other cooler. The lower the surface temperature, the more molecules will be condensed on the surface. By targeting cooled temperature to a sensing chip, selected chemical molecules depending on their boiling temperature would be adsorbed onto the surface.

In some embodiments, the function layer can be used for the purpose of applying a proper DC or AC biasing voltage to the device to attract chemical molecules since many of interested molecules carry positive or negative electric charges. Furthermore, the function layer provides a means to heat the sensing surface to vaporize unexpected/unwanted surface contamination and/or burn out surface contamination. The materials of the conductive layer can be, but not limited to, Ti, Ni, Cr, Pt, Ru, Ni—Cr alloy, NiCrN, Pt—Rh alloy, Cu—Au—Co alloy, Ir—Rh alloy or/and W—Re alloy. The conductive layer can have both good electrical and thermal conductivity, good adhesion to both silicon substrate and metallic sensing surface layer.

In some embodiments, the magnetic field is supplied by the function layer to the sensing chip, or by an external source. In this way, the chemical polar molecules on the sensing surface would have statistically preferred orientation; on the other hand, the chemical polar molecules under test could have their statistically preferred orientation. The effect of applied magnetic field or built-in magnetic materials at function layer is to enhance chemical specific binding, i.e., enhancing chemical molecule adsorption onto the sensing surface, so that to enhance Raman signal. The applied magnetic field can be parallel or perpendicular to the sensing surface. The magnetic field strength is ranging from 0.5 to 3000 gauss, or 2 to 100 gauss.

FIG. 18-21 illustrate a number of examples of the array device. It will be appreciated that the described processes need not to be performed in the order in which they are herein described, but that these descriptions are merely exemplary of preferred methods making the array device. In addition, it is understood and appreciated that the scale of the components and features illustrated in the figures has been exaggerated to facilitate ease of discussion.

Figure 18:
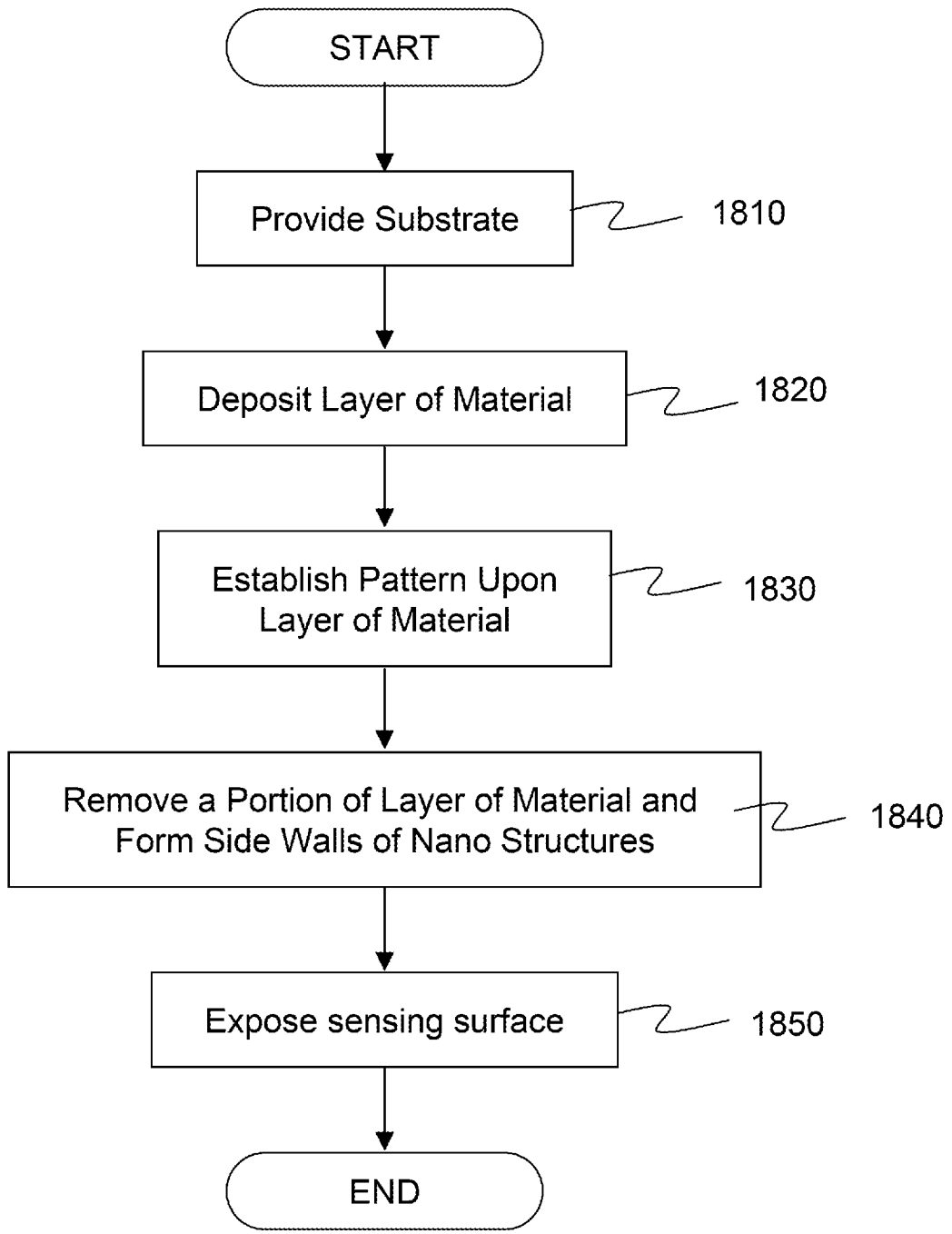
FIG. 18 is a flow chart of a method in accordance with the present invention.

FIG. 18 is a flowchart of a method of forming the array device. As indicated in block 1810, the process is commenced by providing a substrate. In at least one embodiment the substrate is a Si wafer. An inactive material may also be used as the substrate. At least one layer of material is deposited upon the substrate, block 1820. A pattern is then established upon the layer of material, block 1830. The pattern provides areas defining a plurality of nano structures. As in block 1840, a portion of the layer of material are removed, so that side walls of the nano structures are formed. The method further includes forming an exposed sensing surface upon the nano structures, wherein said surface comprises at least one active SERS nano surface and at least one inactive SERS nano surface established in proximity to the active nano SERS surface.

FIGS. 19A-19D provide detailed illustrations for making the nano structures in a sensor array in according to the present invention. The substrate 1900 is made from an inactive material. Alternatively, the substrate can be a non-inactive material with a coating of a layer of an inactive material to provide the inactive SERS nano surface for the completed device.

Figure 19A:
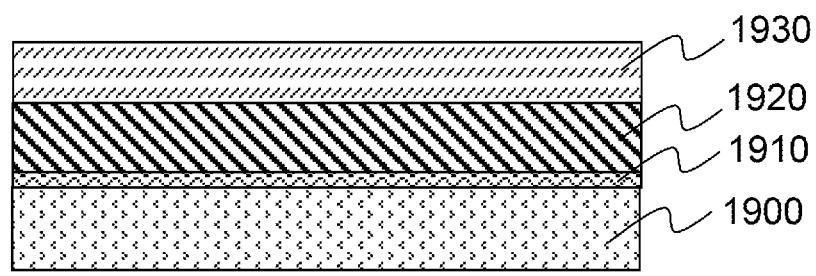
FIGS. 19A-19D show a process for forming an array device in accordance with the present invention.

As shown in FIG. 19A, an optional adhesion layer 1910 is deposited upon the substrate to adhere nano structures onto the substrate. Non-limiting examples of materials for the adhesion layer are Ti and Ni. The thickness of the adhesion layer can be between 10 to 100 nm.

Upon the adhesion layer, a layer of active material 1920 is deposited thereon. The thickness of the active layer 1920 is between 1 nm to 5 μm. In an embodiment, the thickness of the active layer 1920 is between 5 nm to 100 nm. A mask layer 1930 is then deposited on the layer of active material 1920. An example of the mask layer is a layer of photoresist or e-beam resist. An optional metal layer may be established between the resist layer 1930 and active layer 1920 to serve as a hard mask in subsequent processes.

Figure 19B:
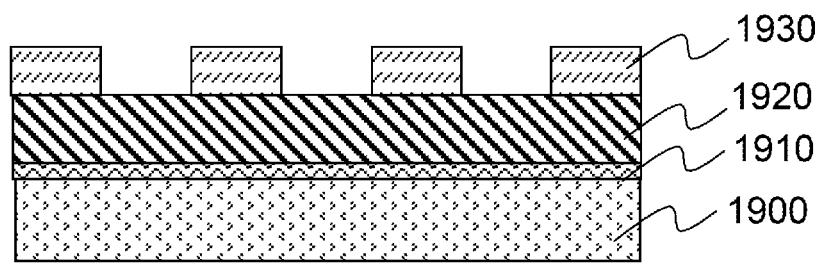

Next, a pattern on the resist layer 1930 is established by a photolithography process or e-beam process (FIG. 19B). Photolithography and e-beam patterning techniques are well known to those skilled in the art and commercially available and need not be described in more detail herein.

Figure 19C:
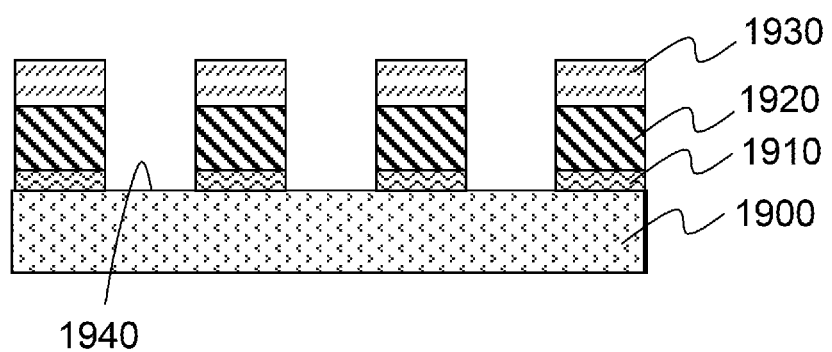
Figure 19D:
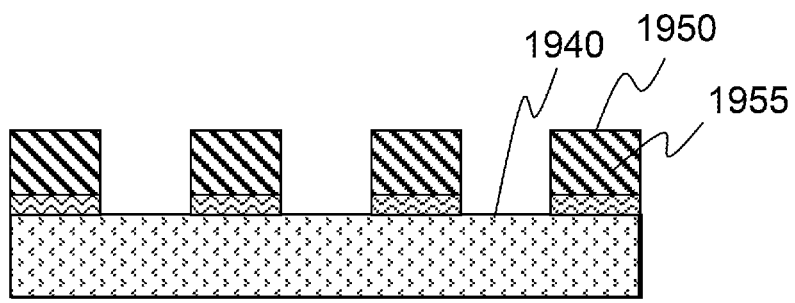

Next, the exposed portion of the active material and the adhesion layer are removed by etching processes such as wet chemical etching or plasma etching (FIG. 19C). The inactive SERS nano surfaces 1940 are formed around nano rods 1955. The remaining mask layer 1930 is finally removed. As shown in FIG. 19D, the completed device has a plurality of nano rods with the active SERS nano surfaces 1950 formed on the top and side wall surfaces of the rods. These active surfaces are surrounded by the exposed inactive SERS nano surface 1940.

In an alternative embodiment, layer 1900 can be an active material and layer 1920 can be an inactive material. The above detailed process can produce a device with an array of nano rods of the inactive material, in which the inactive SERS nano surfaces are surrounded by the active nano SERS surface.

Figure 20A:
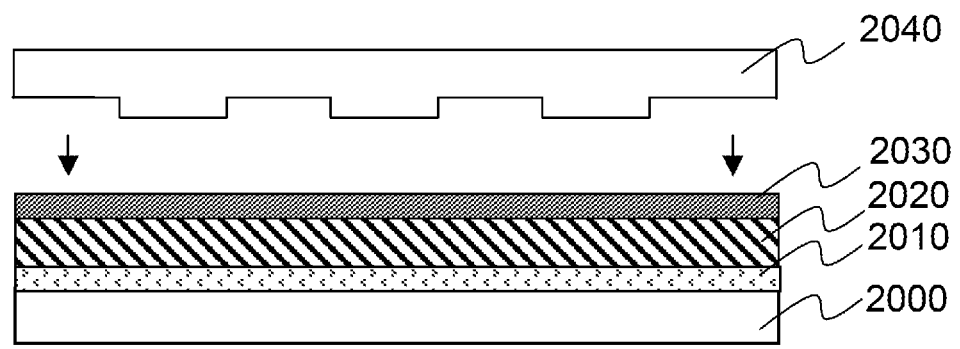
FIGS. 20A-20E show another process for forming an array device in accordance with the present invention.
Figure 20B:
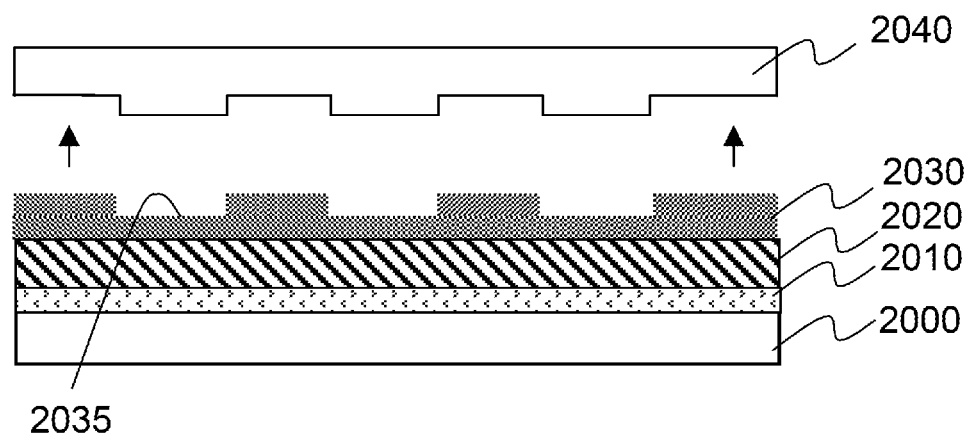
Figure 20C:
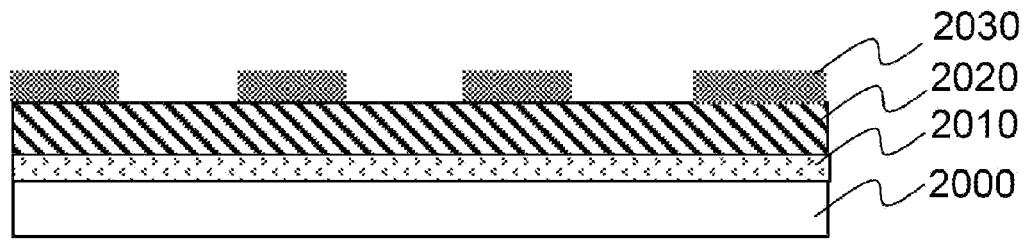
Figure 20D:
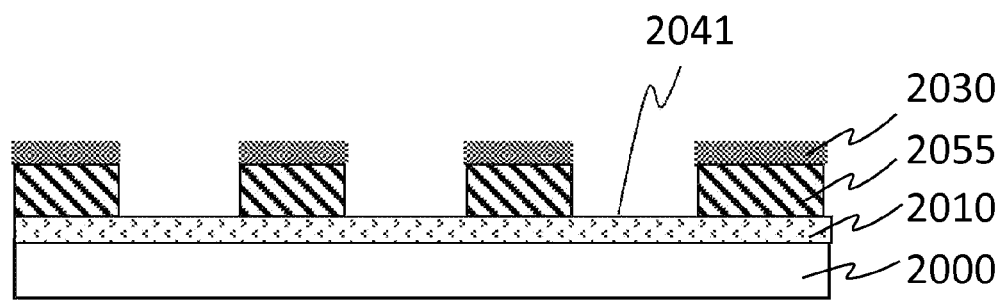
Figure 20E:
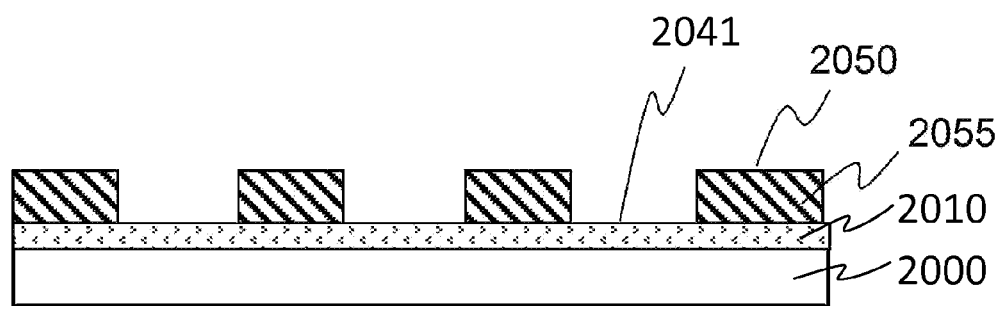

A sequence of steps of yet another embodiment of forming array device is shown in FIGS. 20A-20E. A pattern of the nano structures is defined by an imprint lithography process. The pattern can be produced on a substrate such as a silicon wafer by e-beam lithography and reactive ion etching. The patterned substrate can act as a mold. The pattern in the nano scale is a reverse image of a final nano array. In the first step, a layer of inactive material 2010 may be deposit onto the substrate 2000 to establish the inactive nano SERS surface. A layer of active material 2020 such as Ag or Au is then deposited onto the inactive layer. Then a layer of imprintable material 2030, such as a PMMA or other polymer, is coated on layer 2020. The mold 2040 is then pressed into layer 2030 (FIG. 20A). Imprinting is made during the step after removing the mold (FIG. 20B). In FIG. 20C, pattern transfer is complete using etching to remove residual resist 2035 in the compressed areas. Further chemical etch can be used to etch the metal film in the compressed areas (FIG. 20D). An array of nano surface structure is produced after removing the mask layer. As shown in FIG. 20E, the completed device has a plurality of nano rods with the active SERS nano surfaces 2050 formed on the top and side wall surfaces of the rods. These active surfaces are surrounded by the exposed inactive SERS nano surface 2040.

Figure 21A:
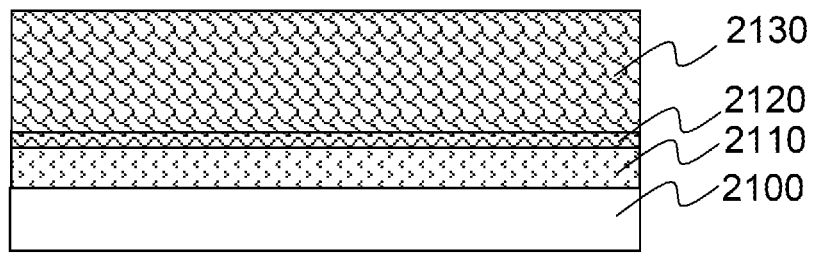
FIG. 21A-21D show yet another process for forming an array device in accordance with the present invention.

In some embodiments, FIGS. 21A-21D show an array of nano structure formed by anodization process. FIG. 21A shows a stack of layers deposited on a substrate 2100. The substrate 2100 may be a silicon wafer. The first layer 2110 is an inactive material. This layer can be 30-50 nm $SiO_2$ made by oxidizing silicon wafers. Above the inactive layer, an adhesion layer 2120 is deposited. The thickness of the adhesion layer is usually controlled in the range of 100 Å-1,000 Å and optimized to provide best adhesion to a noble metal layer, e.g., an Ag or Au layer. The thickness of the adhesion layer 2120 is also optimized for applying an electric bias to the sensing surface for trace chemical detection and further for applying a lower temperature to the sensing surface to enhance sensitivity of trace chemical detection. Above the adhesion layer, an aluminum layer 2130 with a thickness in the range of 0.5-10.0 micrometers, is deposited. Then an anneal operation is performed on the aluminum layer 145 to recrystallize the Al film.

Figure 21B:
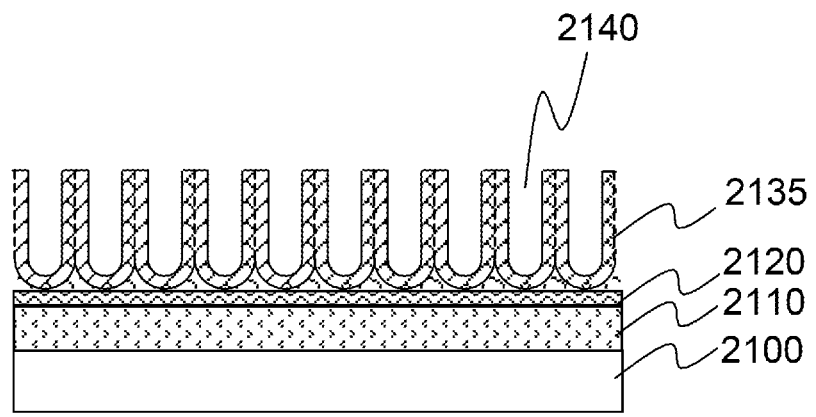

Next, an anodization process is carried out to produce a porous structure 2140 in a form of porous aluminum oxide 2135 (FIG. 21B). In the anodization process, the nano hole or nano rod diameter, the spacing between nano holes or nano rods, D, and the depth of nano hole array or height of nano rod array can be controlled and modified by adjusting operation voltage, current, chemical solution pH value and temperature and process time, etc. The porous structure is formed with naturally self-assembled hexagon-shaped nano pore-array that includes a plurality of pores 2140 surrounded by hexagon-shaped pore wall. Then a wet etch process is performed to widen the pores 2140 and to remove the barrier layer at the bottom of the pores.

Figure 21C:
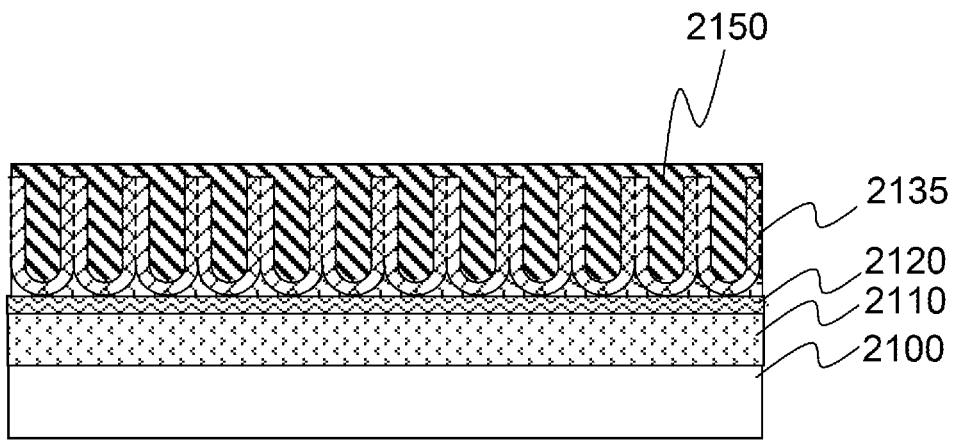
Figure 21D:
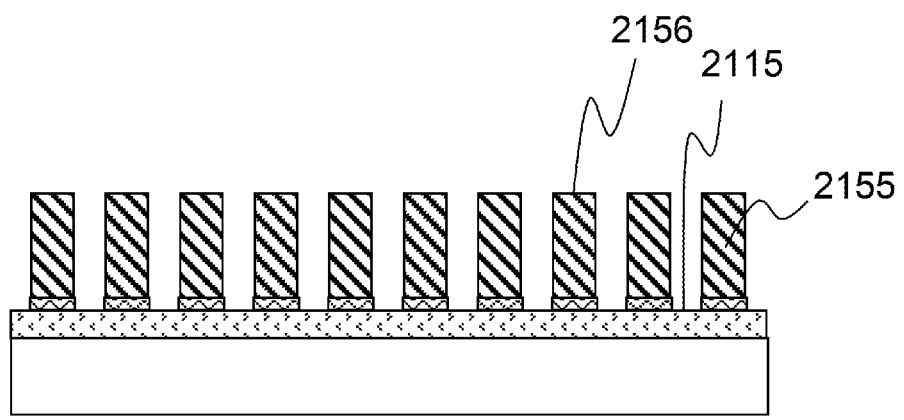

Next, an active material such as a noble metal 2150, such as Ag, Au, or Cu, is deposited to fill the plurality of pores by a physical, chemical, or electro-chemical method (FIG. 21C). A chemical process is then performed to remove the top portion of the noble metal 2150 and the aluminum oxide 2135. A plurality of noble metal columns 2155 are formed on top of the adhesion layer 2120. The exposed portion of the adhesion layer is removed to expose the inactive SERS nano surface 2115 (FIG. 21D). The completed device has a plurality of nano rods with the active SERS nano surfaces 2156 formed on the top and side wall surfaces of the rods. These active surfaces are surrounded by the exposed inactive SERS nano surface 2115.

Figure 22:
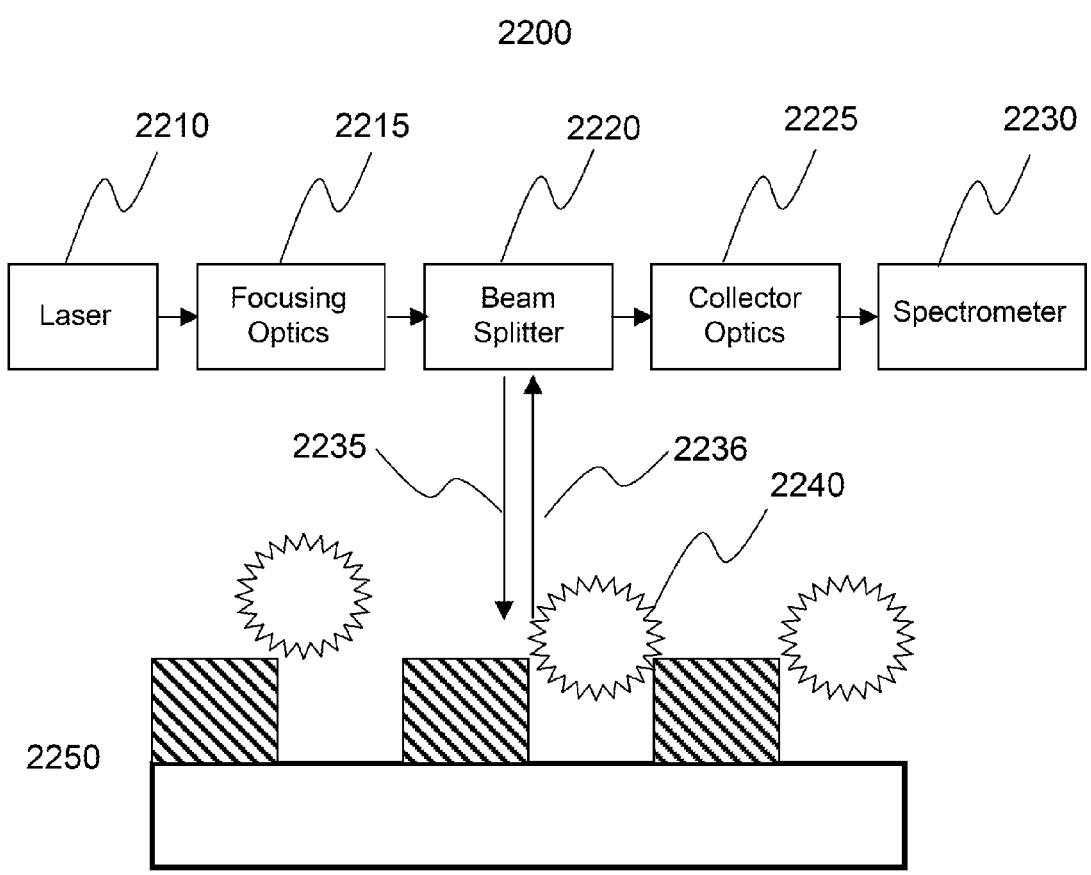
FIG. 22 is a diagram of a SERS system using an array device in accordance with the present invention.

FIG. 22 shows a trace chemical detection system based on the array device in accordance with one embodiment of the present invention. The system includes surface-enhanced Raman spectroscopy (SERS), surface-enhanced Raman resonance spectroscopy (SERRS), surface-enhanced coherent-anti stokes Raman scattering (SECARS), surface-enhanced infrared absorption (SEIRA) spectroscopy, surface-enhanced fluorescence spectroscopy (SEFLS), surface-enhanced photoluminescence spectroscopy (SEPLS), time-resolved above mentioned spectroscopy, other optical spectroscopic methods, and combination of above listed methods, for example, SERS combine with SEFLS or SERS combine with SEPLS, for chemical fingerprint identification and trace chemical sensing.

As shown in FIG. 22, a probe assembly 2200 includes an optical source 2210 such as a laser beam source and an optical assembly 2215 to focus the laser beam. The beam is then deflected by a deflector 2220 to irradiate an array device 2250. The array device 2250 is adsorbed with a chemical substance which is going to be analyzed. Molecules 2240 of the chemical substance adsorbed on the sensing surface of the array device scatter the incoming beam 2235. A portion of the scattered photons 2236 are collected by an optical system. A spectrum analyzer, such as a spectrometer, receives said portion of scattered photons and generates an output indicative of the composition of the chemical substance.

The system illustrated by FIG. 22 can be used in chemical fingerprint identification and trace chemical sensing in the areas of medical/health care, life science, environmental, food safety, forensic, homeland security, etc. For homeland security application at the areas including but not limited to airports, customs, cargos, harbors, trains and train stations, subways, buildings, shopping malls, theaters, resort centers, surface water and other water supply system including wells, the dangerous and harmful chemical compounds can include explosives, nerve agents, blood agents, blister agents, heavy metals and other poison chemicals, e.g., Pb, Cd, Hg, Tl, and arsenic contained compounds, volatile toxins, e.g., benzene, chloroform, pulmonary agents, e.g., phosgene, vinyl chloride, biological agents, toxins, and nuclear weapons. The explosive substances can include TNT, DNT, MNT, DNB, DMNB, EGDN, NG, RDX, PETN, TATP, TATB, HMX, ammonia nitrate, tetryl, picric acid, HNS, etc., and mixtures of two or more items mentioned above, for example, C-4, etc. The dangerous chemical substances also include nerve agents including but not limiting to tabun (GA), sarin (GB), soman (GD), GF, and VX, etc. The blood agents can include cyanides (cyanogen chloride (CK), hydrogen cyanide (AC), potassium cyanide (KCN), sodium cyanide (NaCN), etc.), arsine (SA). The blister agents can include but not limiting to lewisite, phosgene oxime (CX), mustards, etc. The biological agents can include category A agents, e.g., anthrax, smallpox, plagues, category B agents, e.g., Q fever, category C agents, e.g., yellow fever.

The system based on the array device in accordance of the present invention can also be used in chemical fingerprint identification and trace chemical sensing in environmental application, for example, toxic materials monitoring and screening, including but not limited to inorganic and organic nitrites and chlorine contained chemicals, such as NO2- and ClO4-groups and dioxins, benzene and its derivatives, cyanides, heavy metals including but not limited to Pb, Cd, Hg, and arsenic contained compounds, and residue pesticides, and other toxic chemicals in ocean, lake, rivers, reservoir, and wells, and other surface and underground water, as well as in soul and in air.

For environmental protection, the disclosed chemical sensing system can be used for outdoor and indoor pollution monitoring and screening emission sources. Outdoor pollution includes auto vehicle exhaust gas, factory exhaust gas and liquid, etc. Indoor Pollution monitoring and screening in both family houses and workplaces, including but not limited to building, airplane, space shuttle, boat and ship, submarine, and all other areas under the ceiling. Application includes but not limits to monitoring and screening air quality and other health problems associated with plastic floor, wall painting and decoration, painted furniture, plastic household, tools, toys and all other plastic materials indoor which may contain toxic materials, for example, benzene, its derivatives and other volatile organic compounds (VOC), polyvinyl chloride (PVC) and its additives including phthalate, DEHA, and heavy metals, etc.

For medical applications, non-invasive or minimal-invasive early disease diagnosis can be accomplished using the disclosed array device in accordance of the present invention. For example, test through human skin test, eye test, or body fluid test, including saliva, sweat, blood, and urine test, and human breath test to early detect diseases, including but not limited to lung cancer, breast cancer, oral and head cancers, ulcer, bronchial, oesophageal and stomach cancer, colon cancer, skin cancer, diseases of liver, kidney, pancreas, bladder, prostate, uterine, esophageal disease, oxidant stress, eye disease, diabetes, schizophrenia, lipid peroxidation, asthma, tuberculosis, *helicobacter pylori*, etc. Noninvasive or minimal-invasive test can be also applied to diagnose Alzheimer's disease.

The disclosed systems and methods are applicable to urine test by "Smart Toilet" equipped with SERS sensor to early detect diseases, including but not limited to prostate cancer, diseases of bladder, uterine, etc., and to monitoring and screening drugs.

The disclosed systems and methods are applicable to human and animal body fluid test. For example, saliva test for oral cancer, blood test for early disease diagnosis, including but not limit to Alzheimer's disease, HIV, mad cow disease, cardiovascular disease, cancers, and Fast virus and bacteria identification and screening, including but not limited to SARS, bird flu, smallpox, HIV, etc.

Raman diagnosis method can be applied to real time doctor visiting procedure, such as disease screening or special disease diagnosis. In this way, doctor is able to make judgment based on real time Raman test during patient visit, and make on timely decision for necessary medical treatment.

The disclosed systems and methods can be used during surgery, real-time in-line identify cancer tumor portion, rather than usually applied biopsy method which requires time, distinguish the boundary between cancer tumor portion and health portion to real-time support doctor to make decision on cutting location.

The disclosed systems and methods can be used in pharmaceutical applications in medicine R & D, manufacturing and quality monitoring. Raman method can be also applied to medicine taking feedback process. For example, before patient taking medicine and after patient taking medicine at different period of time, Raman test can be carried out to investigation effectiveness from medicine.

The disclosed systems and methods are compatible with a miniaturized Raman sensor with wireless technology used inside human body. For example, a system-on-chip Raman system can be made in a tablet size which includes on-chip mini-laser source, MEMS based mini-spectrometer, wireless module, mini-probe, etc. Initial application will be disease diagnosis of digest system. For example, patient or a person being screened swallows a tablet sized Raman system after his/her digest system got cleaned (similar procedure to that of preparation for colon endoscopy test), Raman scans will be taken timely, for example, from every one minute to every hour a time, then data will be transferred by wireless module, and a computer outside human body will receive Raman data and analyze, search, match, then decision making; next stage of application is minimal invasive with a needle shaped probe head to bring mini-Raman sensor into diagnosis area inside human body, Raman data can be transferred through optic fiber, or wireless module. Applications include but not limit diagnosis of breast cancer, Alzheimer's disease, etc.

The disclosed systems and methods can be used in biotechnology and biomedical applications, such as fingerprint identification of DNA, RNA and protein, DNA sequencing, DNA sorting, etc.

The disclosed systems and methods can be used in forensic applications such as drug test and screening through saliva test, urine test, or powder test; false signature recognition; human identification and screening by DNA profiling; identify microscopic paint fragments, fiber identification, etc. The disclosed systems and methods can be used in drug screening through human body fluid test, or/and breath test by Raman method based on the array device in accordance of the present invention is developed.

The disclosed systems and methods are applicable to food, fruit and beverage monitoring and screening application, monitoring of chemicals in gas, liquid, power, gel, aerosol, or solid phases, including but not limited to ethylene, for stored fruits and vegetables with longer shelf time application; food safety, monitoring and screening harmful chemicals including but not limited residue pesticides (e.g., methamidophos, cypermethrin, deltamethrin, malachite green, etc.), dioxins, illegal artificial additives (e.g., Sudan I, Sudan II, Sudan III, Sudan IV, etc.), food processing by-products (e.g., acrylamide formed from potato chips from processing temperature over 120° C.) by Raman method based on the array device in accordance of the present invention is developed. Those chemicals include but not limit to acrylamide, malachite green, etc. Foods under investigation include but not limit to potato chips, French fries, fried potato, potato crisps, cookies, crackers, cereal products, crisp bread, bread, coffee, prepared toast, roasted nuts, biscuits, chocolates, popcorn, and aquatic products including fish, etc.

The disclosed systems and methods are applicable to identifying and monitoring food packaging processing and preparation materials, including but not limited to identify and screen polyvinyl chloride (PVC) and phthalate materials used as the microwave food wrap, kitchen film, food packaging, processing and preparation materials.

The disclosed systems and methods are applicable to screening counterfeit merchandizes and materials, including but not limited to medicines, drugs, milk-based powders, edible oil, wines, gemstones, currency bills, false signature through inks, art pieces, gasoline, etc.

The disclosed systems and methods are applicable to industrial process quality and production safety monitoring.

Application areas include but not limited to process control for product quality, process and production safety at gas and wet chemical process lines, for example, petroleum refinery plant, chemical engineering manufacturing plant, semiconductor wet chemical process line in clean room, airline and space shuttle, boat, ship and submarine, etc.

The disclosed systems and methods are applied to determine the locations of chemicals. For example, a sensor or sensor network can be placed at different locations including but not limiting to medical doctor clinic office, surgery operation room, shopping center, public resort area, building, custom, road check station, harbor, airport, vehicle, boat and ship, airplane, space shuttle, industrial process site, R&D research lab, quality control office, college lab and office, surface water, well, ground water, hand carried by operation people, and so on.

Chemical sensing application engineering, not only single chemical sensor is placed on site, but chemical sensor net work is designed and arranged to cover application area which all sensors are controlled by sub-central controllers and main-central controller connected with fiber optic or/and wireless system. When abnormal result is found, an alarming signal is automatically triggered in the forms including but not limiting to red color blinking on screen of a computer or PDA, alarming sound in key area, sending alarming E-mail to key people, triggering a phone call to key people cell phone, etc. The abnormal result can be classified into different risk level, for example, green (safe), blue, yellow, orange, red (the most risk).

EXAMPLES

The invention will be further described in the following examples, which do not limit the scope of the invention described in the claims.

Example 1

Fabrication of Nano-Surface Arrays by Anodization Method

A thin film of Ti (about 100 nm) was deposited by e-beam evaporation of Si (100) wafer, followed by the deposition of Ag (about 100 nm). Then a 500 nm Al layer was deposited over the Ag film using physical vapor deposition method.

Then the coated Si wafer was placed into an anodizing bath with 0.3 M oxalic acid solution as the electrolytic solution. The bath was maintained at 10° C., and the anodizing voltage was set at 35 V. After anodization, nano-size narrow pores were formed in the $Al_2O_3$ layer. The diameter of the pores (or holes) can be widened by placing the wafer into a 10 wt. % phosphoric acid solution. The nano pore structure in the $Al_2O_3$ layer acted as a mask for etching active metal layer or depositing active metal layer. Thus a nano surface array was formed after removing oxidized Al layer.

Example 2

Nanoimprint Lithography for Fabrication of Nano-Surface Arrays

The first step in nanoimprint is to press a mold into a thin resist cast on a substrate. The step is to duplicate the nanostructure on the mold in the resist film. The second step is to etch the resist film to form the nanostructure on the substrate.

The mold was patterned with an array of nano dots of 30 nm in feature size using electron beam lithography and reactive ion etching (RIE) on a Si wafer. PMMA was used as the resist on Au coated Si (100) wafer. A thin Ti layer was inserted between Au and Si to improve adhesive. The imprint process was carried out in vacuum at a temperate around 160° C., above the glass temperate of PMMA, at a pressure about 1000 psi. After the pattern from the mole was transferred to the Au coated Si (100), oxygen RIE was used to remove residue resist in the compressed areas in PMMA. Then, the pattern was etched into the Au film. After removing the PMMA, a nano-hole array was formed in Au.

Example 3

1) Demonstration of Nano Array

Figure 24:
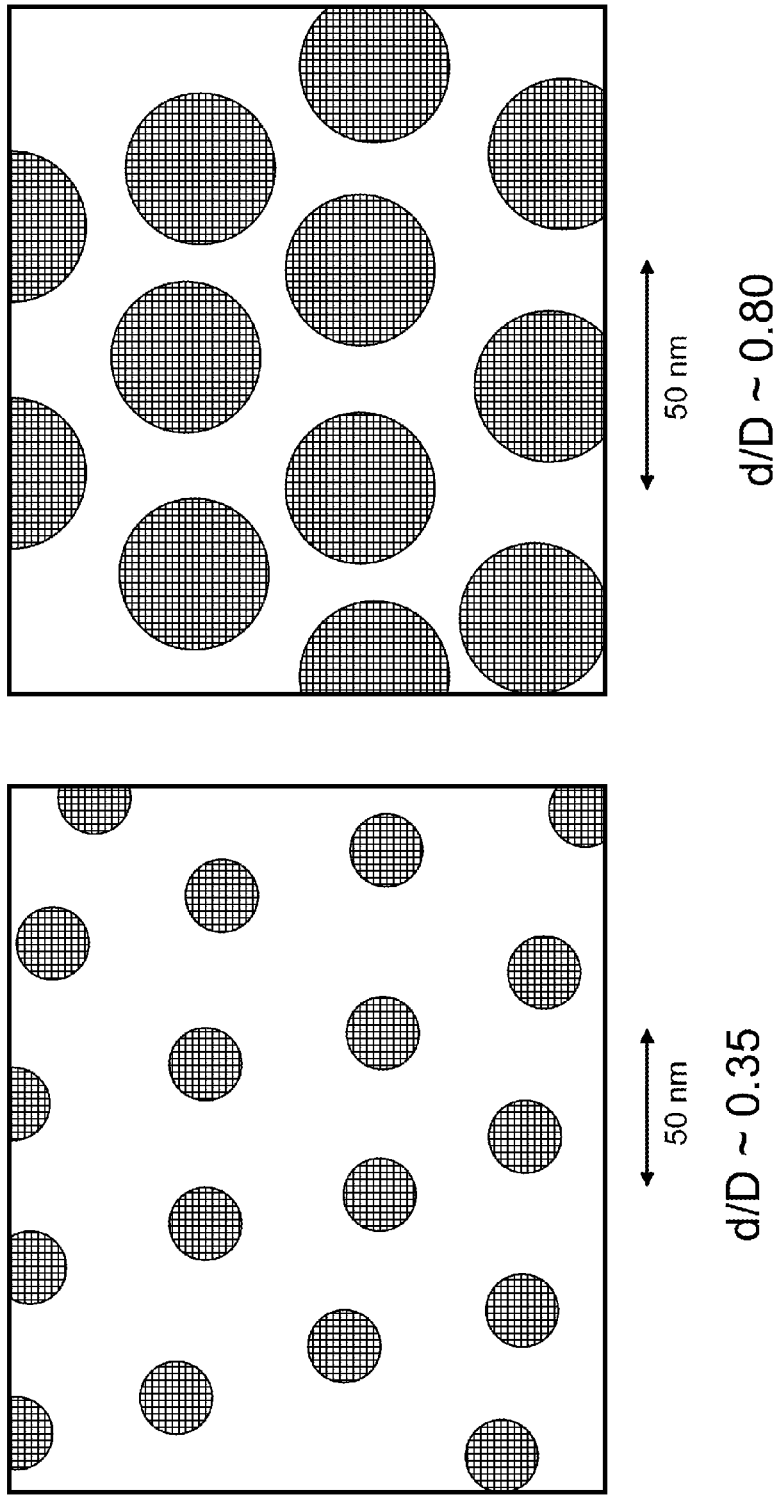
FIG. 24 shows scanning-electron micrographs (SEM) of top-view of a surface structure, where d is the averaged diameter of nano holes, and D is the averaged center-to-center distance between adjacent nano holes.

FIG. 24 is an example of scanning electron microscopy imaging of such nano surface arrays. The left image shows an array of nano-holes with 17 nm diameter and about 30 nm spacing. The image on the right shows an array of nano-holes with 38 nm diameter and about 10 nm spacing.

2) Demonstration of Surface Enhanced Raman Using the Nano-Surface Arrays

Figure 23A:
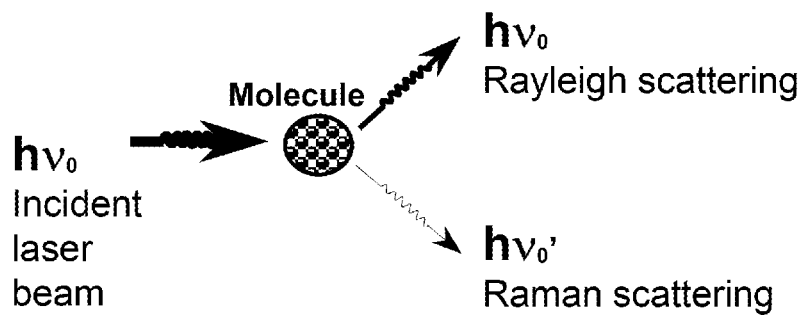
FIG. 23 shows a schematic Raman experiment setup and Raman spectra of various chemicals.
Figure 23B:
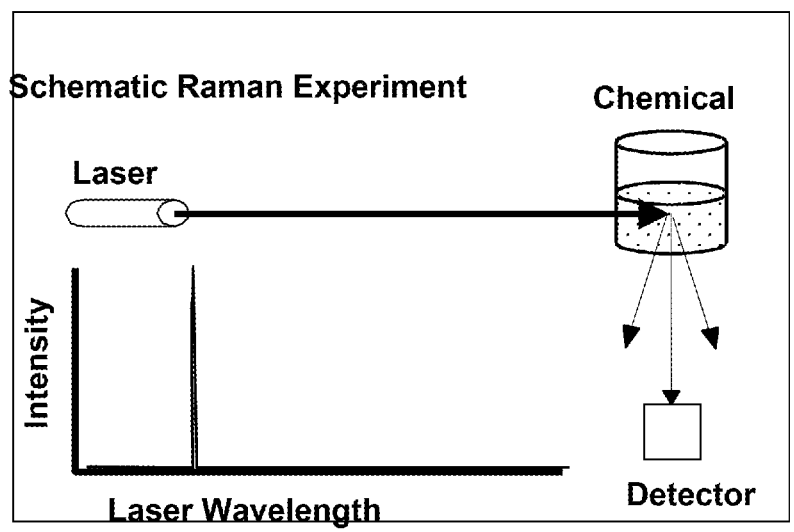

A Raman scattering system, as shown in FIG. 23B, includes a Raman nano-surface array on silicon, a semiconductor laser, which can collect the reflected lights on the surface. The sampling methods include: the array is placed in a solution container or a gas probe cell; or is just lie down horizontally, then to inject liquid chemical onto the surface; or the array is covered by a layer of glass or polymer without physical contact, liquid or gas sample is injected through a microfluidic channel.

Figure 23C:
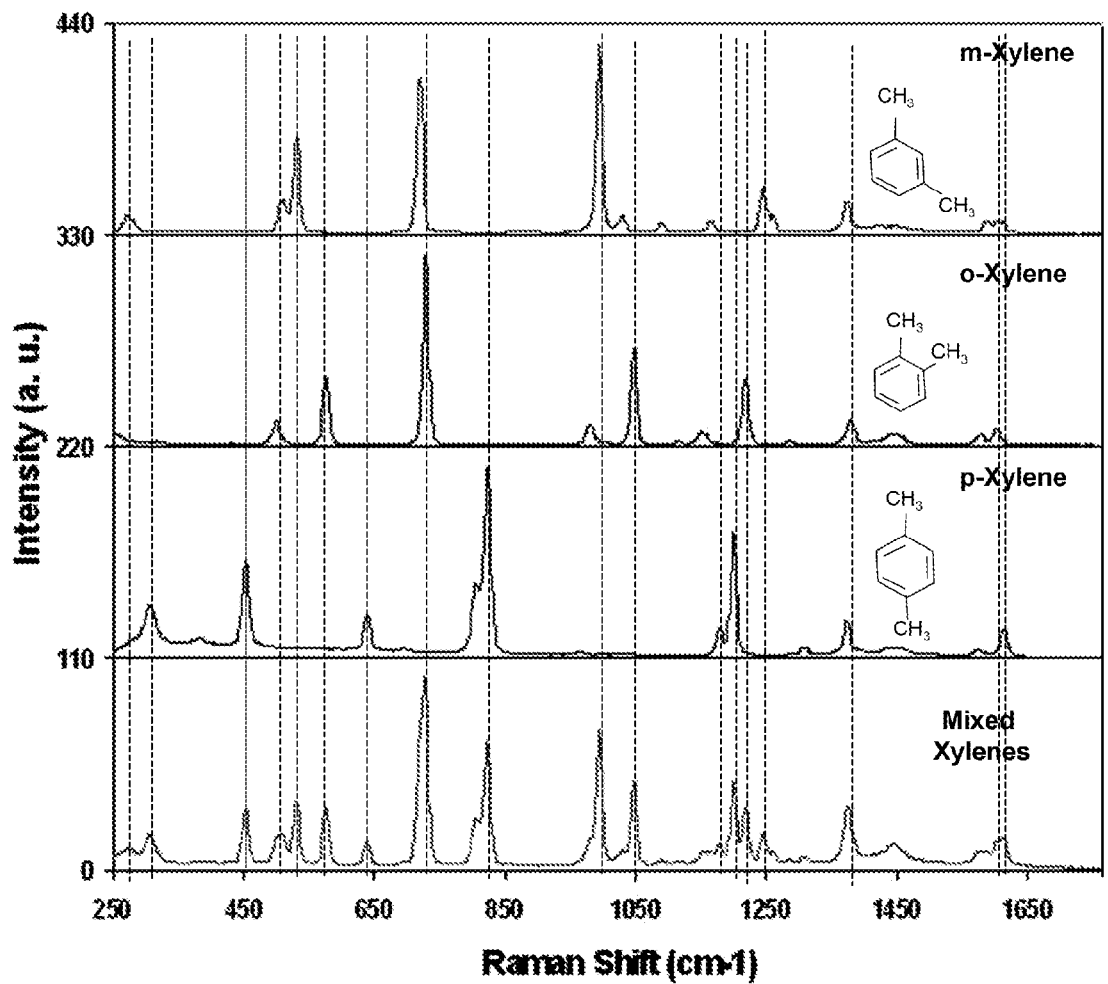

FIG. 23C shows Raman spectra of xylenes. In this example, Raman spectrum of m-xylene, o-xylene, p-Xylene, and mixed xylene are demonstrated separately. As shown in FIG. 23C, each chemical has its own chemical spectral fingerprint, even though the mass of those different xylenes are exact the same. On the other hand, Raman spectrum of mixed xylene shows little interference among those 3 different xylenes. Then, each chemical can be distinctively identified, therefore, Raman methods is one of the best chemical identification ways with spectral fingerprint capability.

Figure 25:
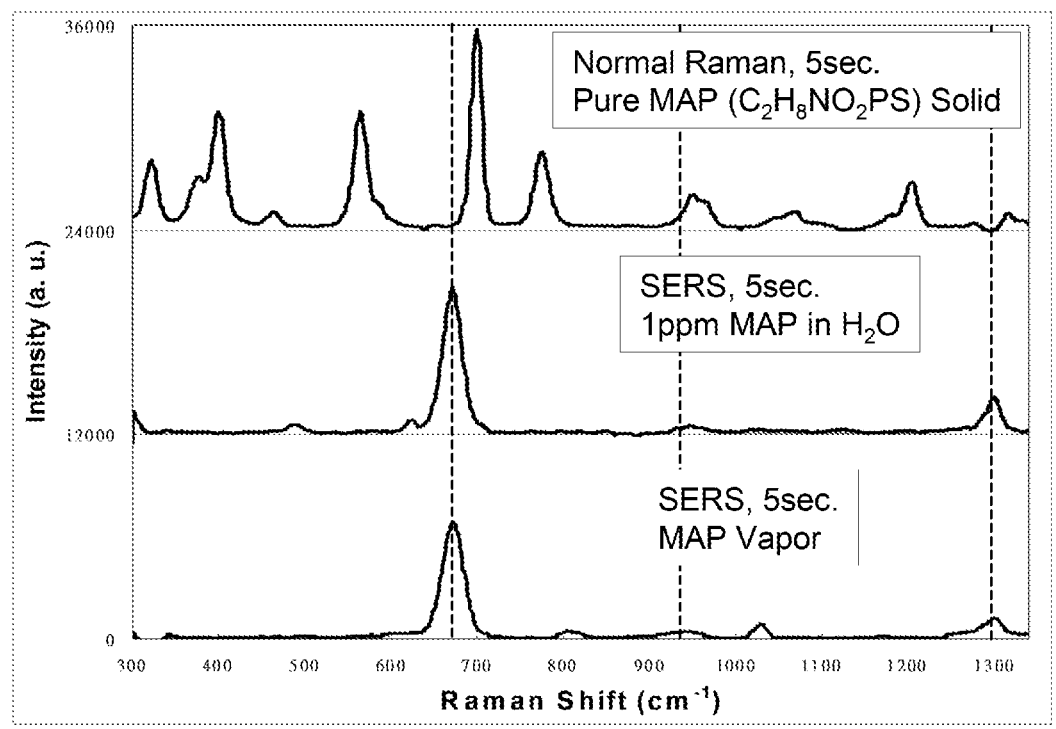
FIG. 25 shows a normal Raman spectrum and a SERS spectrum of methamidophos, a common pesticide and nerve agent stimulant.

Another experiment was carried out using methamidophos (MAP) which is a key pesticide; nerve agent stimulant. A trace amount of the chemical is introduced in liquid phase and vapor phase, respectively. The SERS spectra of these samples are compared against normal Raman spectrum of a pure MAP solid sample. As shown in FIG. 25, both liquid sample and vapor sample show MAP spectrum signature. It demonstrates that MAP vapor detection sensitivity is better than 40 parts per billion (ppb).

Monitoring Network System

In some embodiments, a monitoring network system 2600 includes a central office 2610, a mobile detector 2620, and an analysis lab 2630. The central office 2610 can be operated by a government responsible for food safety, environment monitoring and protection, public health, public security, and crisis preparation and warning agencies, etc. The central office 2610 can be run an independent institution that manages quality control for industrial production of food, drinks, medical drugs, petroleum products, and other industrial products, distribution center for commercial products, etc. The mobile detector 2620 can include a portable detector carried by inspection personnel, or a detector system on a vehicle, which are suitable for collecting and detecting harmful substances in the field. The mobile detector can be positioned at distribution centers for food and other commodities, grocery stores, shopping malls, cinemas or sport facilities, or inspection stations on highways, or at border control, airports, bus stations, subways, and train stations, etc. The mobile detector 2620 includes a probe 2621 and an ID reader 2625.

Figure 26:
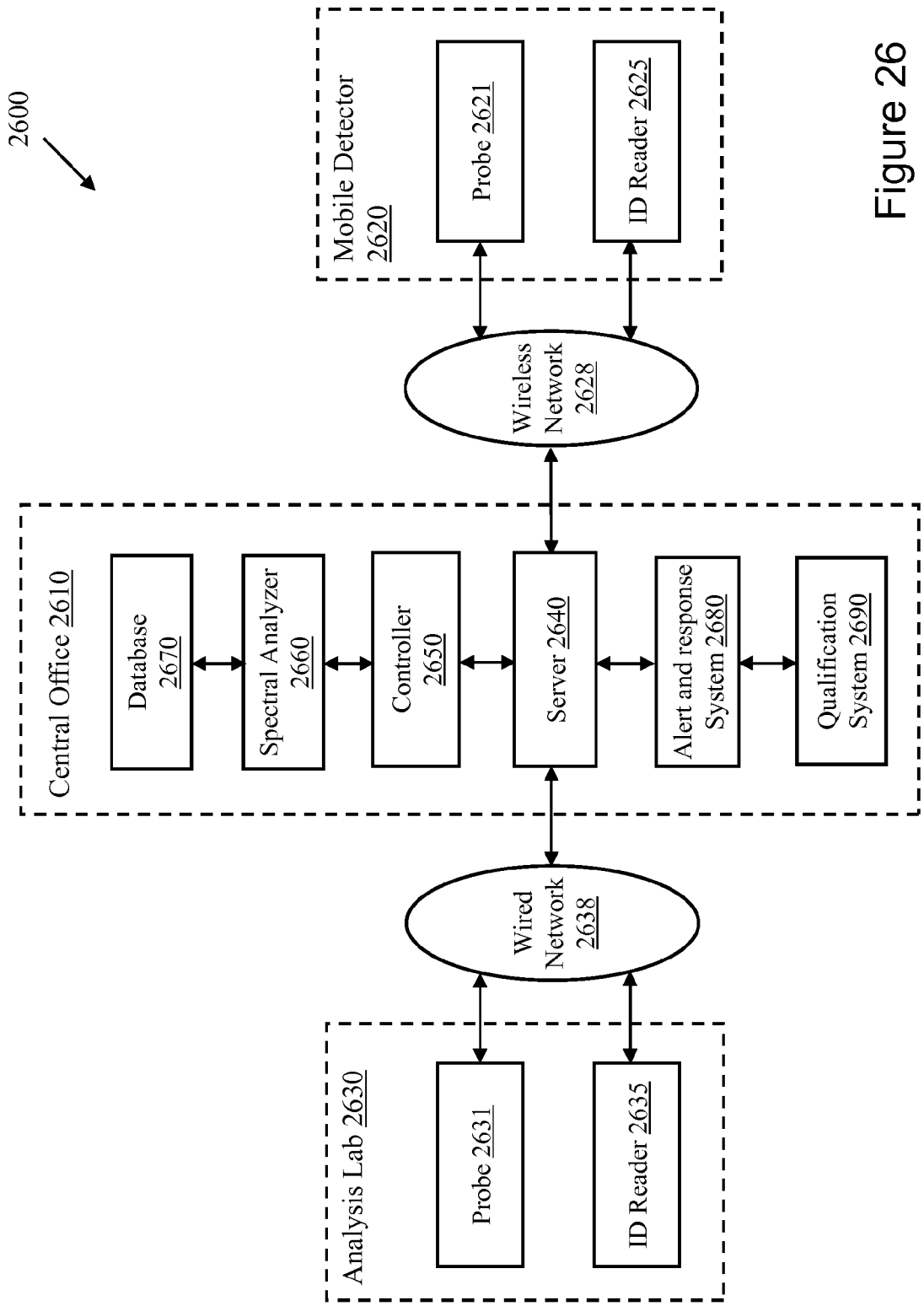
FIG. 26 is a block diagram of an exemplified monitoring network system in accordance to the present invention.
Figure 27:
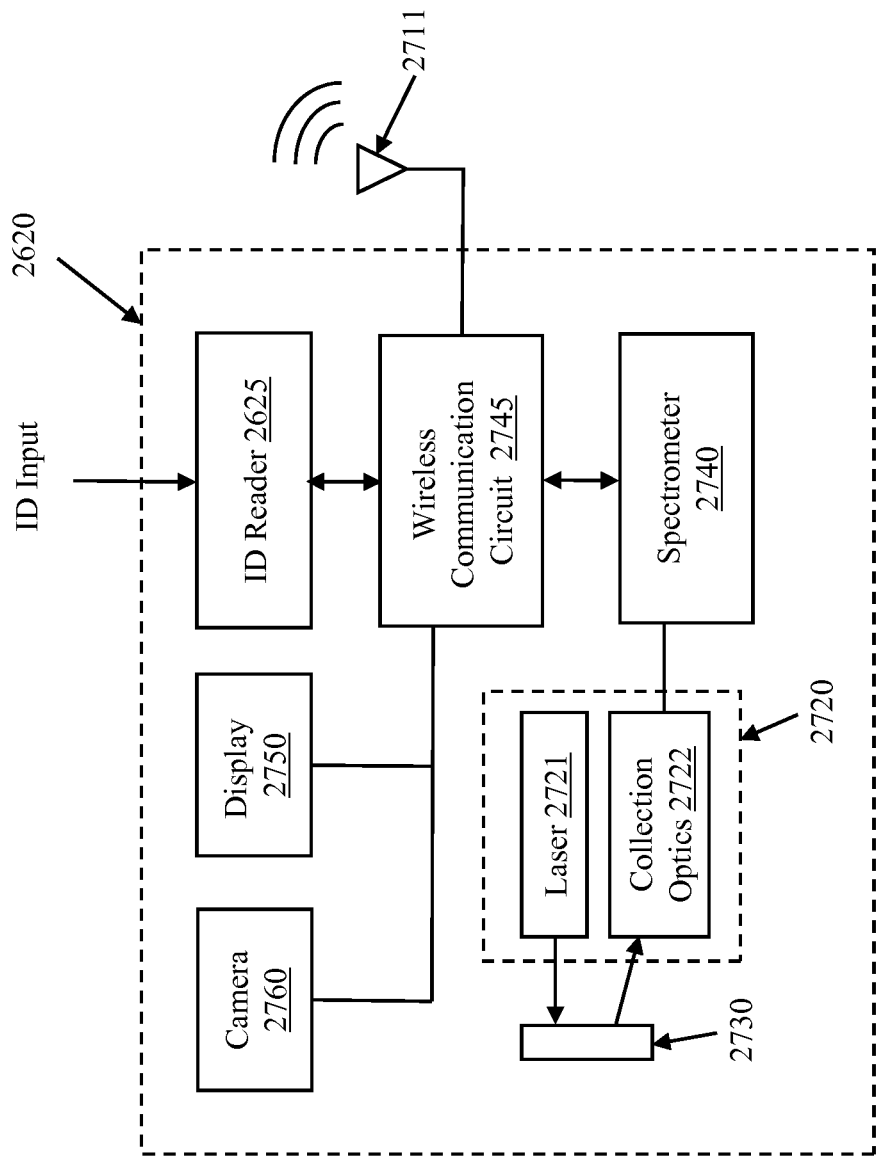
FIG. 27 shows the details of a mobile detector.

The mobile detector 2620, as shown in FIG. 27, can include a probe head 2720 and a sensor 2730 positioned adjacent to the probe head 2720. The sensor 2730A includes nano-structured surfaces that can adsorb molecules of the substance in the sample or in the ambient environment. The nano-structured surfaces in the sensor 2730 can include an array of active SERS nano surfaces and inactive SERS nano surfaces on a substrate or nano particles on a substrate surface, as disclosed above in relation to FIGS. 1-25. The sensor 2730 can also include nano particles in a solution, wherein the sample is introduced in the solution to allow sample molecules to be adsorbed onto the nano particles. The probe head 2720 includes a compact laser 2721 (e.g. a semiconductor laser) configured to illuminate a laser beam on the sample molecules adsorbed on the sensor 2730. The probe head 2720 further includes collection optics 2722 that can collect light scattered from the sample molecules adsorbed on the nano-structured surfaces. The scattered light comprises information about the sample molecules. The probe head 2720 can also include a compact spectrometer 2740 configured to produce a spectrum of the scattered light collected by the probe head 2720. The spectral data is output from the spectrometer 2740 to a wireless communication circuit 2745. The wireless communication circuit 2745 can include an RF transceiver, one or more amplifiers, and impedance matching circuit. The wireless communication circuit 2745 is coupled to an antenna 2711 configured to transmit the spectral data to the central office 2610 via a wireless network 2628 (FIG. 26). The communication can be encrypted in secure protocols.

The ID reader 2625 can be in different formats such as includes non-contact reader such as RFID reading device, a mobile phone, a camera phone, a barcode scanner, an image object recognition system, and a computing device dedicated for inspection and monitoring purposes, etc. The ID reader 2625 can be integrated with the spectrometer 2740 and the probe head 2720, or standalone and in wired or wireless communication with the wireless communication circuit 2745. In some embodiments, the wireless communication circuit 2745 is integrated with the ID reader 2625 (and the display 2750). The spectrometer is connected or in wireless communication with the ID reader 2625.

The ID reader 2625 can receive identification information about the sample such as product model number, batch number, the location of the sampling and substance detection, information about the source of the sample such as the original farm or ranch where the food come from or the manufacturer of a food product, carrier information (e.g. vehicles, trains, ship, airplanes) and the destination of the sample material. The identification can be received in the forms of 1D barcodes, 2D barcodes (i.e. matrix code), alphanumeric numbers, text, etc. The sample ID information is transmitted to the central office 2610 in conjunction with the spectral data of the respective samples. The ID reader 2625 can also receive from the carrier, distributor, or manufacturer of the sample information about pesticide and insecticides applied on the foods being detected, information about animal feeds and antibiotics used on inspected animals and poultries (meat and eggs) and water products.

The mobile detector 2620 can include a display 2750 for displaying instructions for conducting the spectral measurements and messages from the central office 2610. The mobile detector 2620 can include a digital or video camera 2760 which can be combined with the ID reader 2625 or as a separate device. The camera 2760 can take a picture of the commodity that contains the sample material, the vehicle's license number that carries the sample material, the sample or product ID, the driver's license etc. The camera 2760 can also continuously take video images of a site to detect suspicious personnel in correlation with the detection of the harmful materials.

The mobile detectors 2620 can be located within a short range (e.g. within hundreds of yards or a couple of miles) from the central office 2610 to allow wireless signals comprising the spectral data to be communicated in a wireless protocol such as WiMax, WiBro, WiFi, WLAN, 802.11, 802.16, and others. The mobile detectors 2620 can also be located at a long distance from the central office 2610, wherein the wireless signals comprising the spectral data can be communicated using wireless communications standards and protocols such as 3G, 4G, Global System for Mobile communications (GSM), Universal Mobile Telecommunications Service (UMTS), and Code Division Multiple Access (CDMA). GSM can include GPRS, EDGE and CSD. UMTS can include Wideband Code Division Multiple Access (WCDMA), High-Speed Packet Access (HSPA), High-Speed Downlink Packet Access (HSDPA), UMTS-TDD, and Long Term Evolution (LTE). CDMA can include CDMA2000, and Ultra Mobile Broadband (UMB).

Referring to FIG. 26, the analysis lab 2630 can be used for detailed analysis or harmful substances collected from the field or at a large industrial manufacturing sites or distribution center where a high volume of samples need to be analyzed. The analysis lab 2630 can include one or more probes 2631 and one or more ID readers 2635. The probe 2631 and the ID reader 2635 can have structures similar to those illustrated in FIG. 27. The probe 2631 and the ID reader 2635 can communicate with and send spectral data and sample ID information of the samples to the central office 2610.

Figure 28:
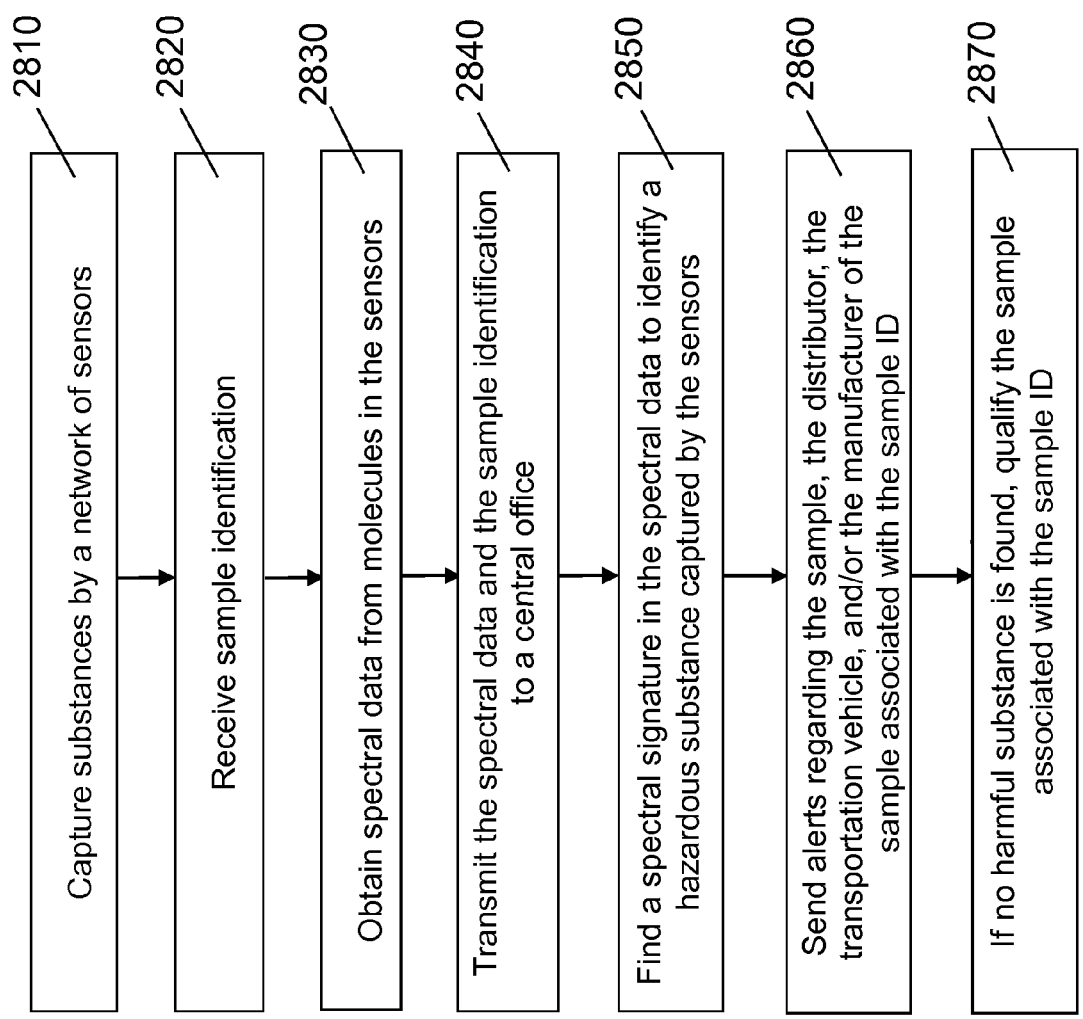
FIG. 28 illustrates an exemplified process for the operations of the monitoring network system.

In some embodiments, referring to FIG. 28, a network of probes can be positioned at grocery stores, shopping malls, transportation stations, border control, a check station on a road, a harbor, an industrial site, a school, or a water source, etc., as described above. Each probe includes a sensor and a probe head. The sensor includes nano structured surfaces to which the molecules can be adsorbed. The probe head is configured to emit a laser beam and collect scattered light from the molecules collected by the sensor. The probe can include a spectrometer for producing spectral data such as Raman spectrum from the scattered light. An ID reader can receive identification information about the sample, the manufacturer, the distributor and carrier of the sample, and/or the destination of the sample.

The sensors in the network capture substances from samples or their perspective environment (step 2810). The samples can include food, drinks, medicine, materials used or produced in manufacturing, water, air, and soil samples from the environment, and samples for forensic and security examinations. The harmful or hazardous substance can include unauthorized additives, residues of pesticides, insecticides and antibiotics in food products, illicit drugs, explosives and flammable materials, a poisonous gas and other harmful chemicals, and contagious virus and bacteria.

Specifically, the sample material can be extracted from a food product such as dairy products, candies, cookies, drinks, alcohol, meat, seafood, tea, fresh or canned vegetables, fruits, grain products, cereals, corn chips, potato chips, or protein containing food. The dairy products can include milk, milk powders, cheese, cheese-containing cakes, yogurts, ice creams, milk containing candies, or cookies, wherein the harmful substance includes melamine, melamine cyanurate, sodium cyclamate, sodium cyclohexylsulfamate, cane sugar, starch, nitrite, nitrate, sulfide, Sudan I, II, III and IV, malachite green, methomidophos, acephate, DDT, DDV, malathion, fenitrothion, malathion, malathion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methyl parathion, phosmet, dimethoate, nitrofuran, furanzolidole, chloramphenicol, chlortetracycline, ciprofloxacin, clenbuterol, ractopamine, enorfloxacin, rhodanmine B, benzoic acid (sometimes found in milk products), hyposulfurous acid, sodium formaldehyde, formaldehyde, phthalates, dioxins, Pd, Cd, Hg, As, and Cr in water, cyanides, chlorates, sulfates, crysoidine G, boric acid and borax, sodium sulfocyanate, lead chrome green, Basic Flavine O, industrial used formaldehyde and NaOH, carbon monoxide, sodium sulfate, industrial surfer, industrial dyes, fructus papaveris, over dosed level of food colorants (e.g. carmine, lemon yellow, allura red AC, sunset yellow, etc.), food preservants, sweeteners (e.g., saccharin sodium salt, Sodium cyclamate), emulsifier (sucrose easter of fatty acid, etc.), swelling agents overdose ($KAlSO_4$, $NH_4AlSO_4$, etc.), bleach, sulfer suffumigation, color protectants (nitrate, nitrite, etc.), $TiO_2$, benzoyl peroxide, olaquindox, chloromycetin, and $KAlSO_4$.

Molecules of the captured substance are adsorbed on the nano structured surfaces of the sensors. The sample identification is next obtained (step 2820). The sample identification can include information that identifies the sample, and the source, distribution channel and method, and the destination of the sample.

Spectral data are next obtained from the molecules adsorbed to the nano structured surfaces of the sensors (step 2830). As described above, a laser beam is emitted by a laser in the probe assembly (such as the one shown in FIG. 22) to illuminate the molecules adsorbed on the nano structured surfaces on a sensor or in a sample solution. Light scattered by the molecules is collected by the probe assembly. The spectral data is obtained from the scattered light by a spectrometer in the probe assembly. An example for the spectral data is Raman spectrum. The nano structured surfaces on the sensor provide surface enhancement to the signal intensity in the Raman spectrum. The substance capture and associated spectral data can be conducted per sample, or periodically (e.g. at 1 min, 10 min, 15 min, or 1 hour intervals).

The spectral data and the sample identification are next transmitted from the sensors to a central office (step 2840) in wired, wireless or other medium. Referring to FIGS. 26 and 28, the central office 2610 can include a communication device such as a server 2640 configured to communicate with the mobile detector 2620 and the analysis lab 2630. A controller 2650 can handle the data to and from the mobile detectors 2620 and the analysis lab 2630, and can control various tasks for a spectral analyzer 2660, a database 2670, the alert and response system 2680, and a qualification system 2690 under predetermined guidelines or policies stored in the database 2670.

The database 2670 stores spectral signatures in association with harmful substances. The spectral analyzer can identify the spectral signatures of known harmful substances in the spectral data, which determines the existence or non-existences of the harmful substances in the samples (step 2850). The results of the spectral analyses are stored in the database 2670 in association with their respective sample IDs under the control of the controller 2650. The database 2670 can store records for different manufacturers, producers, distribution channels, retailers, grocery stores, etc. Problematic entities or locations can be checked more frequently.

If one or more spectral signatures associated with a harmful substance are found in spectral data, the harmful substance is identified in the sample of a product (step 2850). The result is stored in the database 2670. The controller 2650 can ask the analysis lab 2630 to confirm the finding. The controller 2650 can direct the alert and response system 2680 to send out alerts to operators, the mobile detectors 2620 and other mobile devices in the field, to the check points of the distribution channels for the sample products, to the destination of the sample product, or the manufacturing location of the sample product (step 2860). The alert messages can be displayed on the display 2750 in the mobile detector 2620 so that the in-field operator can take appropriate actions such as stopping the shipment of the lot of material containing the detected harmful material. The warning signal can be in the form of emails, text messages, and voice phone call, etc.

The alert and response system 2680 can generate a "high-risk target list" for the detected harmful substance and base materials, and transportation vehicles, distribution channel and production source associated with the detected harmful substance. The "high-risk target list" is stored in the database 2670 to allow the monitoring network system 2600 to more frequently monitor samples on the "high-risk target list" afterwards.

The level of urgency can be categorized by different risk levels such as green (safe), blue, yellow, orange, red (the most risky). The warning signal can include the current and/or anticipated position of the hazardous substance as well as the suspected exterior appearance for the carrier or the package for the hazardous substance. Appropriate personnel can be alerted. Security personnel can be dispatched to the location of the hazardous substance. An evacuation can be initiated.

If a harmful substance is not found in the samples of a product, the qualification system 2690 can qualify the sample as clear of harmful substances; the results can also be stored in the database 2670 for the record (step 2870).

In some embodiments, the location and time of the hazardous/harmful substance can be correlated by the positions of the sensors and the capture times for the detections of harmful substance. The location for a stationary hazardous material can be determined by interpolating the positions of the sensors. The locations and capture times of a moving sample containing the hazardous substance can be generate a moving path to predict the destination of the sample to allow it to be intercepted.

In some embodiments, the spectral data collected by the sensors can be used in conjunction with image data captured from the scene near the spectral sensors. For example, a digital or video camera 2760 positioned near the probe can take a picture of a suspected person or a package. The image of the suspected person or package can be stored and reported in association of the location of the hazardous substance to prepare for an appropriate response.

The above disclosed systems and methods have wide applications. In one example, a distribution center for meat, vegetables, fruits, and other food products can include a central office (as shown in FIG. 26) and multiple inspection personnel each carrying (or wearing) a mobile detector. The distribution center can include an analysis lab or can use the services of an analysis lab off site. The food products such as vegetables, dairy products, meat and vegetables can be shipped into the distribution center by big trucks (e.g. 20 ton trucks) from food manufacturing sites, vegetable, orchards, farms, dairy farms, ranches, etc. The inspection personnel can retrieve the identification of each food product, driver and vehicle information, and the source and destinations of the product. The inspection personnel can visually inspect the food product, and take samples of the incoming food products for spectral detection as the products are offloaded from the big trucks. The identification information and the spectral data are wirelessly transmitted instantaneously to the central office for spectral analysis. The data is stored in the database. The food products that pass the inspection will be qualified. The food products are then separated into small batches and loaded onto smaller trucks (e.g. 2 ton trucks) to be shipped to retail sites such as grocery stores, supermarkets, restaurants, and large retail stores such as Costco, Wal-Mart, or Target. The problematic products can be held for further analysis in the analysis in the lab. If harmful substance is confirmed, the food products can be stopped or destroyed. Since the identification information is stored, the source of the food is immediately known. Inspection personnel can be sent to the site that produced the food product, and alert messages can be sent to other distribution centers that may have received food products from the same source.

In another example, the disclosed monitoring system can be used to monitor and to prevent the spread of infectious diseases such as SARS in wide area. The disclosed monitoring system can be used to monitor pollutants in the environment, and to monitor chemical and biological agents for preventing and defending against terrorist attacks. For example, the disclosed monitoring system can be disposed in a water distribution system including reservoirs, canals, water treatment plants, and rivers. The disclosed monitoring system can be used to sense chemical changes in the environment for forecasting earthquakes or monitoring chemical changes for action taken after earthquakes.

In some embodiments, the probe 2621 in the mobile detector 2620 and the probe 2631 in the analytical lab 2630 can include other types of sensors. For example, the probe 2621, 2631 can include a chemical or biological immunoassay for detecting harmful biological and chemical substances. The biological immunoassay is configured to hold a plurality of antibodies which each is specifically configured to bind with a target antigen which may be part of or associated harmful biological and chemical substance. Likewise, the biological immunoassay can hold a plurality of antigens which each is specifically configured to bind with a target antibody which may be part of or associated harmful biological and chemical substance. The binding of a specific pair of antigen-antibody in the biological immunoassay can be detected by spectral analysis such as Raman spectroscopy as a positive identification of the harmful antigen or antibody substance. A spectral signature can indicate the binding of one of plurality of antibodies with the specific antigen.

Figure 29:
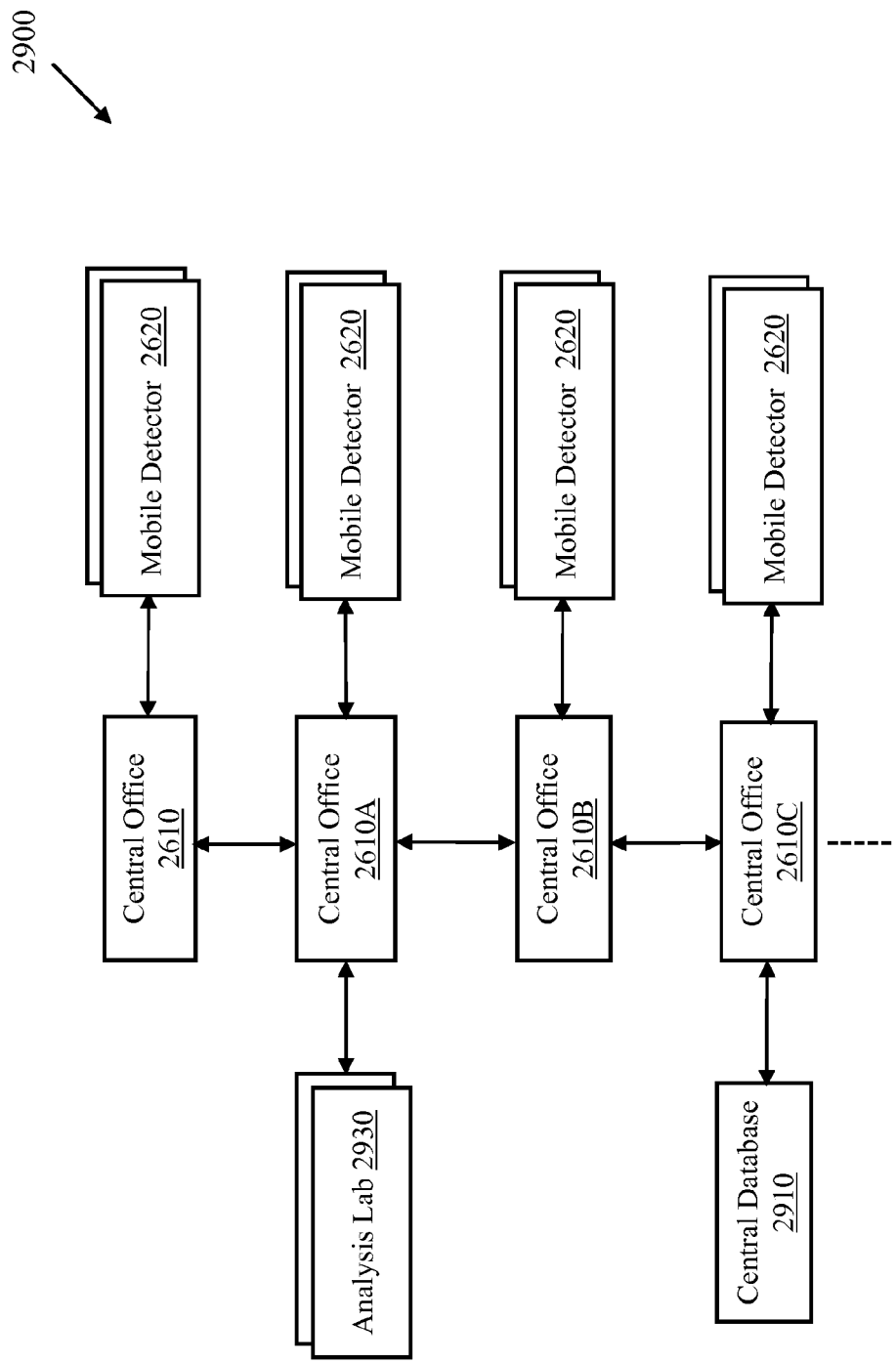
FIG. 29 is a block diagram of another exemplified monitoring network system in accordance to the present invention.

In another example, the probe 2621 in the mobile detector 2620 and the probe 2631 in the analytical lab 2630 can use enzyme inhibition method. Vegetables often include residuals of pesticides which may include organic phosphorus Inhibition of enzymes by the organic phosphorus can be detected by spectral analysis such as Raman spectroscopy. A spectral signature can indicate the inhibition of the enzyme by a harmful substance in the sample material, which is used as an indication to detect the residual pesticides in vegetables and fruits. In some embodiments, referring to FIG. 29, a monitoring network system 2900 can include a network of central offices 2600, 2600A, 2600B . . . , each in communication with mobile detectors 2620 or stationary detectors. The monitoring network system 2900 can include one or more analysis lab 2930 in wired or wireless communication with the central offices 2600, 2600A, 2600B . . . . The monitoring network system 2900 can include a central database to track inspection data from all central offices 2600, 2600A, 2600B . . . so that the data can be cross shared between the central offices which can cover a large region such as a a state, a province, a country, a district, a city, a inspection station or a mobile vehicle. The controllers and processors in the central offices 2600, 2600A, 2600B . . . can process data in a cloud computing model. The qualification and warning can be implemented in region wide. A region-wide alert and response system is in communication with the plurality of central offices. The alert and response system is configured to send out an alert signal about the sample material when the harmful substance is identified in the sample material in one or more of the central offices.

The monitoring network system 2900 can include different stages of inspections: the first stage inspection of harmful substances: using on-site and high throughput detection methods, such as Raman and surface-enhanced Raman methods, enzyme inhibition method, and chemical or biological immunoassay method, to screen high volume high distribution-rate goods (for example: food, drinks, water, drug raw materials, body fluid samples of human being or animals, etc.) in distribution channels, storage areas and logistics distribution centers. Small quantity of the samples (e.g. 0.1%-1% of the samples) can be sent to the analytical lab 2630. The analytical lab 2630 can have other lab equipment such as HPLC, GC-MS, IC, IMS, AAS, ICP-MS, etc., for additional analyses for confirming the existence of the harmful substance.

The monitoring network system 2900 can include different authorized levels: a first level at inspection point (test station or inspection mobile vehicle), a second level that connect inspection points at the first level by a network, a $3^{rd}$ level of city monitoring and control center, a $4^{th}$ level of county monitoring and control center, a $5^{th}$ level of the province/state monitoring and control center, and a $6^{th}$ level of central government monitoring and control center. The monitoring network system 2900 can track the detected harmful substance back to its distribution channels and production sources, so that event monitoring and control center is able to find impact channels and areas as function of time, in order to take immediate action to minimize impact from the event. In should understood that the foregoing description and examples, limited and narrow interpretation of descriptive language intended to better illustrate the invention is not to be construed as limiting in any way nor to limit the scope of the invention contemplated by the inventor. It will be clear that the invention may be practiced otherwise than as particularly described in the foregoing description and examples. Numerous modifications and variations of the present invention are possible in light of the above teachings and, therefore, are within the scope of the appended claims.

What is claimed is:

1. A monitoring network system for inspecting and controlling harmful substances, comprising:
   a plurality of probe assemblies each comprising:
      a sensor comprising nano structured surfaces, configured to adsorb molecules of a sample material captured adjacent to the sensor;
      a laser configured to emit a laser beam to illuminate the molecules adsorbed to the nano structured surfaces;
      a spectrometer configured to produce spectral data from light scattered by the molecules adsorbed to the nano structured surfaces; and
      a ID reader configured to retrieve identification information about the sample material; and
   a central office in communication with the plurality of probe assemblies, comprising:

a computer storage configured to store one or more spectral signatures each associated with a harmful substance and the identification information for the sample material;

a communication device configured to receive the spectral data and the identification information from the plurality of probe assemblies;

a spectral analyzer configured to determine, in the spectral data, a spectral signature matching at least one of the spectral signatures stored in the computer storage thereby to identify, in the sample material, the harmful substance associated with the one of the spectral signatures; and an alert and response system in communication with the spectral analyzer, wherein the alert and response system is configured to send out an alert signal about the sample material when the harmful substance is identified in the sample material.

2. The monitoring network system of claim 1, wherein the identification information comprises a product model number, a batch number, a location where the sample material is collected, the source of the sample, and the distribution, and destination of the sample material.

3. The monitoring network system of claim 1, wherein the central office further comprises a controller configured to calculate a location the sample material at a specific a time using the spectral data obtained from two or more of the plurality of probe assemblies and using the locations of the two or more of the plurality of probe assemblies.

4. The monitoring network system of claim 1, wherein the plurality of probe assemblies are installed in or around a building, an airport, a custom, a conveyance system for cargo or luggage, a doctor or a health advisor's office, a check station on a road, a harbor, in a vehicle, a ship, a submarine, an airplane, a train, a subway, an industrial site, a resort area, a shopping mall, a research Lab, a school, or a water source.

5. The monitoring network system of claim 1, wherein the spectral data comprises a Raman spectrum.

6. The monitoring network system of claim 1, wherein the nano structured surfaces in the sensor comprise three dimensional structures each having a width between about 1 nm and about 300 nm.

7. The monitoring network system of claim 6, wherein the plurality of nano structures include at least one of recesses, nano rods, or nano holes on a substrate, or nano particles in a solution.

8. The monitoring network system of claim 6, wherein adjacent nano structures have spacings between about 1 nm and about 1000 nm.

9. The monitoring network system of claim 6, wherein the nano structures have heights between about 1 nm and about 1000 nm.

10. The monitoring network system of claim 1, wherein the sensor comprises a substrate and wherein the nano structured surfaces comprise nano particles introduced on the substrate.

11. The monitoring network system of claim 1, wherein the nano structured surfaces in the sensor comprise:

an active material having active nano surfaces; and
an inactive material having inactive nano surfaces in proximity to the active nano surfaces, wherein the active nano surfaces have widths between about 1 nm and about 300 nm.

12. The monitoring network system of claim 11, wherein the sensor comprises
a substrate comprising the inactive material; and
a first layer comprising an active material over the substrate, wherein the first layer includes a plurality of recesses that expose the substrate.

13. The monitoring network system of claim 11, wherein the active material comprises a metallic material.

14. The monitoring network system of claim 11, wherein the active material is selected from a group consisting of Ag, Au, Cu, Pt Al, Fe, Co, Ni, Ru, Rh, and Pd.

15. The monitoring network system of claim 11, wherein the inactive material comprises an insulator.

16. The monitoring network system of claim 15, wherein the inactive material is selected from a group consisting of silicon dioxide, aluminum oxide, silicon nitride, tantalum oxide, and titanium oxide.

17. The monitoring network system of claim 12, wherein the sensor further comprises an adsorption layer on the first layer.

18. The monitoring network system of claim 17, wherein the adsorption layer comprises a material selected from a group consisting of $TiO_2$, $SiO_2$, $Al_2O_3$, $Si_3N_4$, $Ta_2O_5$, ZnO, Zr oxide, Hf oxide, Y oxide, Ag oxide, Au oxide, Sn oxide, Sb oxide, a metal doped with chlorine or chloride, and a polymeric material.

19. The monitoring network system of claim 1, wherein the sample material is extracted from a food product.

20. The monitoring network system of claim 19, wherein the harmful substance comprises melamine, sodium cyclamate, sodium cyclohexylsulfamate, cane sugar, starch, nitrite, nitrate, sulfide, Sudan I, II, III and IV, malachite green, methomidophos, acephate, DDT, DDV, malathion, fenitrothion, carbofuran, brodifacoum, tetramethylenedisulfotetramine, sodium fluoroacetate, fluoroacetamide, chlorphacinone, pindone, diphacinone, amitraz, monocrotophos, phorate, disulfoton, phosmet, parathion, fenthion, phosphamidon, diazinon, aldicarb, trichlorfon, aldrin, bentazone, deltamethrin, cypermethrin, methyl parathion, phosmet, dimethoate, nitrofuran, furanzolidole, chloramphenicol, chlortetracycline, ciprofloxacin, clenbuterol, ractopamine, enorfloxacin, rhodanmine B, benzoic acid, hyposulfurous acid, sodium formaldehyde, formaldehyde, phthalates, dioxins, Pd, Cd, Hg, As, and Cr in water, cyanides, chlorates, sulfates, crysoidine G, boric acid and borax, sodium sulfocyanate, lead chrome green, Basic Flavine O, industrial used formaldehyde and NaOH, carbon monoxide, sodium sulfate, industrial surfer, industrial dyes, fructus papaveris, over dosed level of food colorants, food preservants, sweeteners, emulsifier, swelling agents overdose, bleach, sulfer suffumigation, color protectants, $TiO_2$, benzoyl peroxide, olaquindox, chloromycetin, or $KAlSO_4$.

21. The monitoring network system of claim 1, wherein the harmful substance comprises an explosive material, a flammable material, a narcotic drug, a poisonous gas, a radioactive material, or contagious virus and bacteria.

22. The monitoring network system of claim 1, wherein the sample material comprises a body fluid obtained from a person or an animal, wherein the one or more spectral signatures are associated with a disease or an illicit drug use in the person or an animal based on the spectral signature.

23. The monitoring network system of claim 1, wherein the central office further comprises a qualification system configured to qualify the sample material, wherein the database is configured to store the qualification status in association with the identification information.

24. The monitoring network system of claim 1, wherein the ID reader in at least one of the plurality of probe assemblies comprises an RFID reading device, a mobile phone, a camera phone, a barcode reader, and a computing input device.

25. The monitoring network system of claim 1, wherein the computer storage is configured to store a high-risk target list of entities that produce, transport, distribute, or sell the harmful substance identified in the sample material to allow the plurality of probe assemblies to more frequently track and monitor these entities.

26. A monitoring network system for inspecting and controlling harmful substances, comprising:
a plurality of probe assemblies each comprising:
a sensor comprising nano structured surfaces, configured to adsorb or bind with molecules of a sample material captured adjacent to the sensor;
a laser configured to emit a laser beam to illuminate the molecules adsorbed to the nano structured surfaces;
a spectrometer configured to obtain spectral data from light scattered by the molecules adsorbed to the nano structured surfaces; and
a ID reader configured to retrieve identification information about the sample material;
a plurality of central offices that are connected in a computer network, wherein each of the central offices comprises:
a computer storage configured to store one or more spectral signatures each associated with a harmful substance and the identification information for the sample material;
a communication device configured to receive the spectral data and the identification information from one or more of the plurality of probe assemblies; and
a spectral analyzer configured to determine, in the spectral data, a spectral signature matching at least one of the spectral signatures stored in the computer storage thereby to identify, in the sample material, the harmful substance associated with the one of the spectral signatures; and
an alert and response system in communication with the plurality of central offices, wherein the alert and response system is configured to send out an alert signal about the sample material when the harmful substance is identified in the sample material in one or more of the plurality of central offices.

27. The monitoring network system of claim 26, wherein the computer storage is configured to store a high-risk target list of entities that produce, transport, distribute, or sell the harmful substance identified in the sample material to allow the plurality of probe assemblies to more frequently track and monitor these entities.

28. The monitoring network system of claim 26, wherein the sensor comprises nano structured surfaces, wherein the nano structured surfaces in the sensor comprise three dimensional structures each having a width between about 1 nm and about 300 nm, wherein the plurality of nano structures include at least one of recesses, nano rods, or nano holes on a substrate, or nano particles in a solution.

29. The monitoring network system of claim 26, wherein the sensor comprises a biological immunoassay configured to receive a plurality of antibodies each configured to bind with a specific antigen in or associated with the harmful substance, wherein the spectral signature indicates the binding of one of plurality of antibodies with the specific antigen.

30. The monitoring network system of claim 26, wherein the sensor comprises an enzyme, wherein the spectral signature indicates the inhibition of the enzyme by a harmful substance in the sample material.

* * * * *